(12) United States Patent
Bango et al.

(10) Patent No.: US 11,804,033 B1
(45) Date of Patent: Oct. 31, 2023

(54) MICROBIOLOGICAL B-CAPTCHA TO IMPROVE ARTIFICIAL INTELLIGENCE PATHOGEN IDENTIFICATION

(71) Applicants: Joseph Bango, New Haven, CT (US); Michael Dziekan, Bethany, CT (US)

(72) Inventors: Joseph Bango, New Haven, CT (US); Michael Dziekan, Bethany, CT (US)

(*) Notice: Subject to any disclaimer, the term of this patent is extended or adjusted under 35 U.S.C. 154(b) by 0 days.

(21) Appl. No.: 17/685,118

(22) Filed: Mar. 2, 2022

Related U.S. Application Data

(63) Continuation-in-part of application No. 15/732,259, filed on Oct. 16, 2017, now Pat. No. 11,300,484.

(60) Provisional application No. 63/155,568, filed on Mar. 2, 2021.

(51) Int. Cl.
*G06T 7/00* (2017.01)
*G06V 10/774* (2022.01)
*G06T 7/11* (2017.01)

(52) U.S. Cl.
CPC ........ *G06V 10/7747* (2022.01); *G06T 7/0012* (2013.01); *G06T 7/11* (2017.01); *G06T 2207/10056* (2013.01); *G06T 2207/20081* (2013.01)

(58) Field of Classification Search
CPC ..... G06V 10/7747; G06T 7/0012; G06T 7/11; G06T 2207/10056; G06T 2207/20081; G06T 7/0014; G06T 2207/10061; G06T 2207/20084; G06F 2221/2133
USPC ............ 73/863.02, 1.01, 865.9, 866; 702/85, 702/104, 97; 356/243.1, 243.4, 243.5
See application file for complete search history.

(56) References Cited

U.S. PATENT DOCUMENTS 9,644,230 B2 * 5/2017 Hammond ............. G01N 15/14
10,796,150 B2 * 10/2020 Ganssle ................. A01G 22/00
11,137,384 B2 * 10/2021 Yoon ..................... A61B 5/0082

* cited by examiner

*Primary Examiner* — Robert R Raevis
(74) *Attorney, Agent, or Firm* — Michael A. Blake

(57) ABSTRACT

A method of testing identification of pathogens for a biological Completely Automatic Public Turing Test To Tell Humans And Computers Apart (bCAPTCHA) system comprising: automatically electing a first electronic image for a participant with a computing system, where said electronic image comprises an image of a biological pathogen; presenting options for participant to select to identify characteristics of the pathogen; processing responses from participant. A method of testing identification of pathogens for a biological Completely Automatic Public Turing Test To Tell Humans And Computers Apart (bCAPTCHA) system comprising: automatically electing a first electronic image for a participant with a computing system, where said electronic image comprises an image of a biological pathogen; presenting options for participant to identify the pathogen; processing responses from participant.

15 Claims, 22 Drawing Sheets

FIG. 1

Electrospray Ionization Process of Bio-Aerosol Species, with nanopore analysis

FIG. 2

210 Cathode Ray Tube
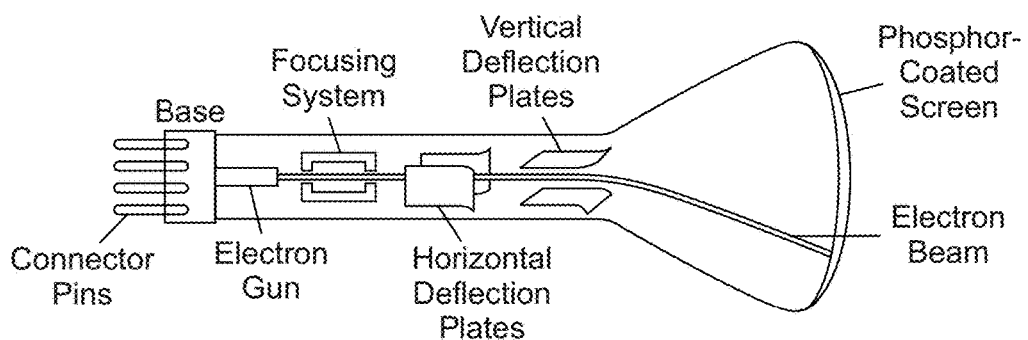
220 Charged Particle Detection Delivery System
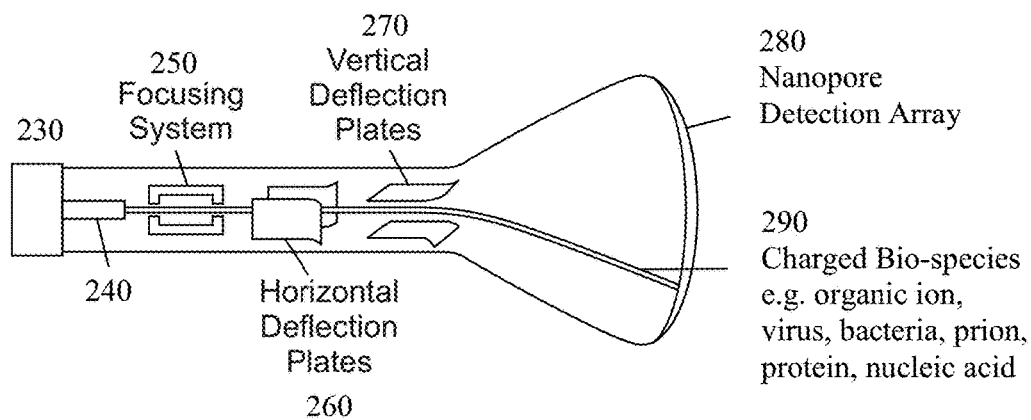
FIG. 5

300

310

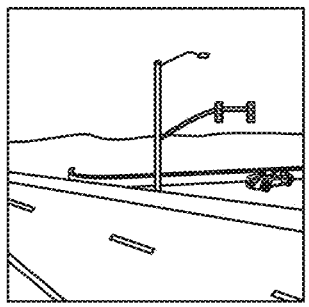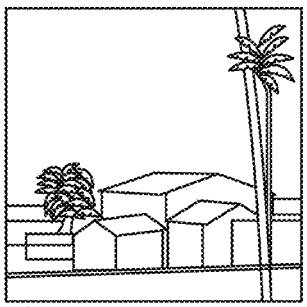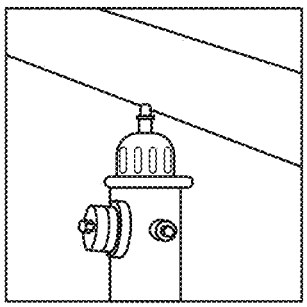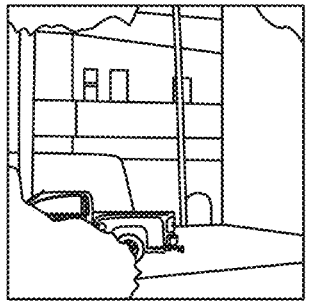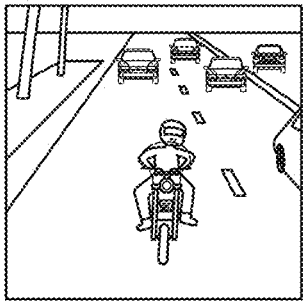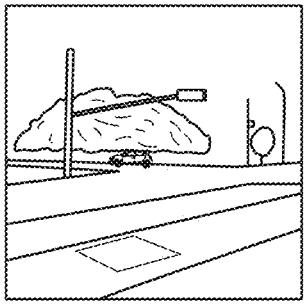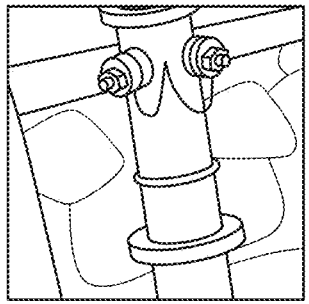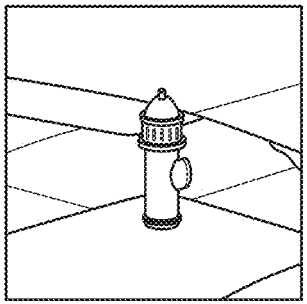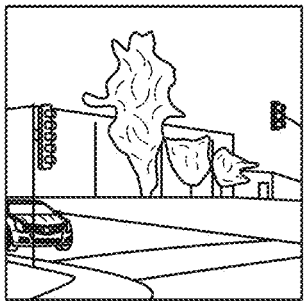
FIG. 10

| =IF(B4=$B$1),"MATCH","_")) | | |
|---|---|---|
| A | B | C |
| | Negative ▾ | |
| Scientific Name | Cell Wall (Gram Stain) ||
| Acinetobacter Baumannii | Negative | MATCH |

FIG. 18

`=IF (AND(G4="MATCH", H4=$I$1), "MATCH", IF (AND(G4="MATCH", H4="Pleo"), "MATCH", "_"))`

| A | B | C | D | E | F | G | H | I |
|---|---|---|---|---|---|---|---|---|
| Scientific Name | Cell Wall (Gram Stain) | | Presence or Absence of Capsule | | Shape | | Arrangement | |
| Acinetobacter Baumannii | Negative | MATCH | Capsule | MATCH | Bacillus | MATCH | Mono | MATCH |

FIG. 19

`=IF(AND(I4="MATCH", J4=$J$1), "MATCH", "_")`

| A | B | C | D | E | F | G | H | I | J | K |
|---|---|---|---|---|---|---|---|---|---|---|
| Scientific Name | Cell Wall (Gram Stain) | | Presence or Absence of Capsule | | Shape | | Arrangement | | Flagella or Cilia | |
| Acinetobacter Baumannii | Negative | MATCH | Capsule | MATCH | Bacillus | MATCH | Mono | MATCH | Cilia | MATCH |

FIG. 20

`=IF(AND(K4="MATCH", L4=$L$1), "MATCH", "_")`

| A | B | C | D | E | F | G | H | I | J | K | L | M |
|---|---|---|---|---|---|---|---|---|---|---|---|---|
| Scientific Name | Cell Wall (Gram Stain) | | Presence or Absence of Capsule | | Shape | | Arrangement | | Flagella or Cilia | | Type of Cilia | |
| Acinetobacter Baumannii | Negative | MATCH | Capsule | MATCH | Bacillus | MATCH | Mono | MATCH | Cilia | MATCH | Type IV Pili | MATCH |

=F(AND(K4="MATCH",N4=$N$1),"MATCH","_")

| A | B | C | D | E | F | G | H | I | J | K | L | M | N | O |
|---|---|---|---|---|---|---|---|---|---|---|---|---|---|---|
|   | Negative ▾ |   | Capsule ▾ |   | Bacillus ▾ |   | Mono ▾ |   | Cilia ▾ |   | Type IV Pili ▾ |   | Lophotrichous ▾ |   |
| Scientific Name | Cell Wall (Gram Stain) | Presence or Absence of Capsule | | Shape | | Arrangement | | Flagella or Cilia | | Type of Cilia | | Type of Flagella | | |
| Acinetobacter Baumannii | Negative | MATCH | Capsule | MATCH | Bacillus | MATCH | Mono | MATCH | Cilia | MATCH | Type IV Pili | MATCH | N/A | |

FIG. 23

=F(or(O4="match",N4="Match"),A4,F(and(K4="MATCH",J4="None",J4=$J$1),A4,""))

| A | B | C | D | E | F | G | H | I | J | K | L | M | N | O | P |
|---|---|---|---|---|---|---|---|---|---|---|---|---|---|---|---|
|   | Negative ▾ |   | Capsule ▾ |   | Bacillus ▾ |   | Mono ▾ |   | Cilia ▾ |   | Type IV Pili ▾ |   | Lophotrichous ▾ |   |   |
| Scientific Name | Cell Wall (Gram Stain) | Presence or Absence of Capsule | | Shape | | Arrangement | | Flagella or Cilia | | Type of Cilia | | Type of Flagella | | Results | |
| Acinetobacter Baumannii | Negative | MATCH | Capsule | MATCH | Bacillus | MATCH | Mono | MATCH | Cilia | MATCH | Type IV Pili | MATCH | N/A | | Acinetobacter Baumannii |

MICROBIOLOGICAL B-CAPTCHA TO IMPROVE ARTIFICIAL INTELLIGENCE PATHOGEN IDENTIFICATION

CROSS-REFERENCES

This patent application is a continuation-in-part of patent application Ser. no. 15/732,259, by Joseph J. Bango, entitled "METHOD FOR ANALYSIS OF AEROSOLIZED BIOLOGICAL SPECIES IN EPIDEMIC AND PANDEMIC PREDICTION", filed on Oct. 16, 2017, the entire contents of which are fully incorporated by reference herein. This patent application also claims the benefit of provisional patent application no. 63/155,568, by Joseph J. Bango and Michael Dziekan, entitled "MICROBIOLOGICAL b-CAPTCHA TO IMPROVE ARTIFICIAL INTELLIGENCE PATHOGEN IDENTIFICATION", filed on Mar. 2, 2021, and which provisional application is fully incorporated by reference herein.

TECHNICAL FIELD

The present invention relates generally to using captcha techniques to improve artificial intelligence learning systems, and more particularly, to a using a captcha approach to improve artificial intelligence systems with respect to identification of pathogens.

BACKGROUND

There is an urgent need, in a post pandemic world, to identify the emergence of future airborne pathogens to be able to predict the next epidemic before a new pandemic can arise. One of the problems in any potential worldwide diseases monitoring system, is finding a way to sift through the massive data to identify all of the bacteria and viruses floating around. While physical tests of microorganisms are an essential part of the identification process, artificial intelligence offers a valuable option to augment the process of decision analysis of what a given pathogen might be based on morphological and other characteristics. Currently, artificial intelligence systems cannot identify various pathogens with a high or even good rate of success.

Thus, there is a need for a microbiological captcha to improve artificial intelligence pathogen identification that overcomes the above listed and other disadvantages.

SUMMARY OF THE INVENTION

The invention relates to a method of testing identification of pathogens for a biological Completely Automatic Public Turing Test To Tell Humans And Computers Apart (bCAPTCHA) system comprising: automatically electing a first electronic image for a participant with a computing system, where said electronic image comprises an image of a biological pathogen; presenting options for participant to select to identify characteristics of the pathogen; processing responses from participant.

The invention also relates to a method of testing identification of pathogens for a biological Completely Automatic Public Turing Test To Tell Humans And Computers Apart (bCAPTCHA) system comprising: automatically electing a first electronic image for a participant with a computing system, where said electronic image comprises an image of a biological pathogen; presenting options for participant to identify the pathogen; processing responses from participant.

BRIEF DESCRIPTION OF THE DRAWINGS

The present disclosure will be better understood by those skilled in the pertinent art by referencing the accompanying drawings, where like elements are numbered alike in the several figures, in which:

FIG. 1 is a diagram of an electrospray capture process for biological trace species from the air;

Figure 2:
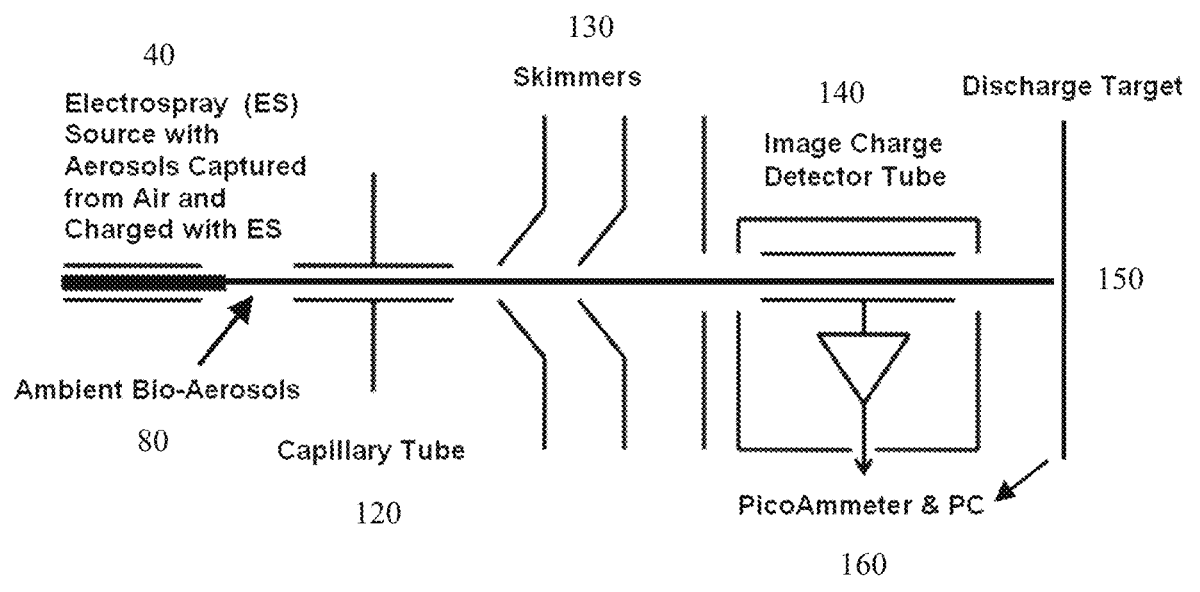

FIG. 2 is a schematic of a charge detection mass spectrometer with a target that consists of a nanopore detector;

FIG. 5 is schematic drawing of a charged particle delivery system and a cathode ray tube;

FIG. 10 is a drawing of a reCAPTCHA icon;

FIG. 15 is a drawing of a bacteria and an inscribed area that is zoomed in on;

FIG. 18 is drawing of a screenshot showing a match for a gram stain;

FIG. 19 is a drawing of a screenshot showing a match for an arrangement;

FIG. 20 is a drawing of a screenshot showing a match for an flagella or cilia;

FIG. 21 is a drawing of a screenshot showing a match for a type of cilia;

FIG. 22 is a drawing of a screenshot showing a not applicable for a type of flagella;

FIG. 23 is a drawing of a screenshot showing a match for an *Acinetobacter baumannii*;

DETAILED DESCRIPTION OF THE INVENTION

Figure 3:
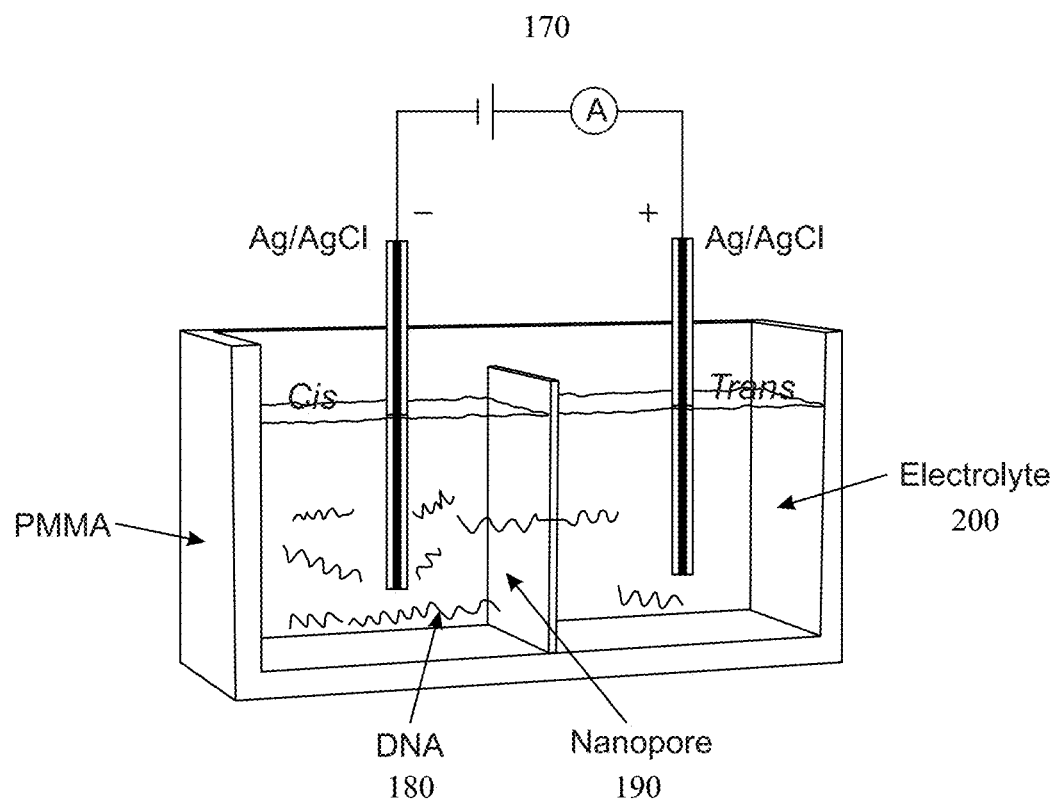
FIG. 3 is a schematic of a nanopore nucleotide detection device.

Method for Analysis of Aerosolized Biological Species in Epidemic and Pandemic Prediction The disclosed invention provides a means to perform both surveillance and forecast of public health and force protection pathogen threats, and specifically, viral outbreaks. The enabling tool for the achievement of these goals is the machine that will collect and analyze the captured viruses. Then, predictions, feedbacks and control measures can inhibit the evolution of an outbreak assuming that there are the means and the will to act. Having an almost real-time tool to measure viral load of air at condensed areas is an ideal situation for public policy makers since they could evaluate immediately and accurately the impact of a decision. A near real-time atmospheric viral/selective bioaerosol sampler and genetic sequencer is proposed. In many instances, an outbreak is caused by what is referred to as "patient zero", the person who is the original carrier of a specific disease. If the "patient zero" can be found more quickly, or at least "pathogen zero" found more quickly, government agencies such as the CDC (Centers for Disease Control) or WHO (World Health Organization) can quickly identify potential sources of new epidemics. While the proposed sampler obviously cannot identify a specific vector or patient-zero for a viral agent, the technology promises to yield previously unattainable data on the emergence and spread of new virulent agents. This information can also be utilized by pharmaceutical companies to create flu vaccines that are created for specific regions where a known type of pathogen exists, specific to that genome. By using this information, flu manufacturers will be less dependent essentially educated guesses at what type of pathogen is "out in the wild", so its effectiveness will be much greater, and production response time shortened considerably.

Reference may be made to the new so-called 'Cancer Moonshot' effort in the U.S. to address solving cancer riddles. Of all the recommendations from the research community thus far, none has been more dominant than utilizing the benefits of the virtual cloud. Cloud computing enables large-scale collaborative analysis. "Two of the 10 recommendations specifically call for a direct patient engagement network and the creation of adult (and pediatric) immunotherapy clinical trials networks. However, collaboration is at the core of all 10 recommendations, as the Blue Ribbon Panel unequivocally calls for better data sharing. The scale of the data used in cancer discovery means computation has a huge role in supporting research. Every sequenced genome requires 300-400 GB of hard disk space just to store the raw and processed files. By 2025, the amount of human genomic data is predicted to be 2-40 exabytes, exceeding the storage requirements of astronomy and YouTube. To overcome these challenges, the cancer research community is increasingly turning to the cloud to store and analyze cancer genomic data. The U.S. National Cancer Institute (NCI) initiated Cancer Genomics Cloud Pilots to enable researchers to access The Cancer Genome Atlas (TCGA)—the world's largest public genomic data set—containing over 2 petabytes of sequencing and other data from more than 11,000 patients. Rather than waiting weeks to download the data, researchers can log in to a cloud-based system to explore the data and run large-scale analyses. A key value of the cloud is that collaboration is default; researchers can log in to the NCI Pilots from anywhere in the world and work together on a project".

In the proposed final configuration, distributed viral air samplers will be 'seeded' in areas of human congestion, such as airports and other mass transit locations around the world. Ambient air will be continuously drawn into the sampler, and larger fractions filtered out until only specific bio-aerosols are left. These bio-aerosols, specifically of interest influenza virions, become charged ions after interaction with an electrospray source. Using a combination of electrostatic filtration and charge detection spectrometry, target virions are accumulated and subjected to continuous genetic sequencing via an Oxford Nanoprobe analyzer or other suitable sequencer. The viral (or other bioaerosol of interest) concentration and genetic sequence data is uploaded via sampler internal telemetry to the cloud via RF or broadband Internet connectivity. The data collected by these 'bio-nodes' is then used as part of an improved probability algorithm for predicting the outbreak of a given viral strain in a given region, and for worldwide infectious disease monitoring. The successful implementation of the proposed technology could be to epidemiology what GPS has meant to navigation in its impact on humanity.

OVERVIEW OF THE INVENTION

Detecting Viral Pathogens in Near Real Time:

Computational software promises to help stem the spread of disease that can decimate civilian populations, and incapacitate military forces. Because of the time constant between when an individual becomes exposed and infected to an airborne pathogen such as influenza, and when that individual becomes symptomatic may be many days (1-4 day incubation period), vector transmission to other persons will likely have occurred. Only a small fraction, generally the very young or the very old, in the early stages, will end up in a hospital or clinic where positive identification of the virus has been obtained and is available as a statistic. Being able to monitor the level of viral load in a local population outside of the hospital or clinic setting, coupled with an ability to know precisely what the genome sequence of the virus is, would advance the state-of-the-art in epidemic predictive capability substantially. We believe we may be able to achieve this goal through the merging of several well-established technologies, and the combination of several new developments in gene sequencing.

Influenza, as well as many bacterial agents, can survive for hours as an airborne species. Because droplets from a cough or sneeze encapsulate many virions, the probability for disease transmission in congested public areas is very high. In general, particles that are between less than 5 microns can remain airborne for many hours and the smaller the particulate, the longer the residence time. As a mucosal enveloped packet of virions moves through the air, evaporation of water (90% water, 0.5-5% high molecular weight glycoproteins) causes the droplet to become smaller and thus more mobile. Residence time is enhanced if the humidity level is high, and if there is a lack of direct sunlight. The research lab of Dr. Bourouiba at MIT has investigated the fluid dynamics of disease transmission, and has determined experimentally that cough ejecta and sneeze cloud last typically approximately 250 milliseconds can literally shoot across a room in a matter of seconds, 200 times farther than previously thought.

Emerging or re-emerging viral and bacterial infectious diseases (e.g. H1N1, H5N1, SARS, tuberculosis) have increasingly high human and economic consequences (IMF/ World Bank 2006). Confined environments, such as airplanes, hospitals and schools, serve as mixers where pathogens can stay suspended and spread from host to host. Hence, understanding the dynamics of pathogens indoors is critical to improving the modeling and control of epidemics (Settles 2006; Tang et al. 2006; Weber & Stilianakis 2008). Nevertheless, the transmission mechanisms of even the most common respiratory diseases remain poorly understood. Three modes of transmission are discussed in the medical literature. Self-inoculation may arise through direct contact with the mucus (or other bodily fluids) of an infectious subject. Large droplet transmission may arise through the spraying of infected droplets directly onto the conjunctiva or mucus of a susceptible host via coughing or sneezing. Airborne transmission may arise through inhalation of relatively small infected droplets or the pathogen-bearing solid residues of size <5-10 μm, referred to as droplet nuclei, that can form from the small droplets via evaporation (e.g. Nicas, Nazaroff, & Hubbard 2005; Tellier 2006). The first two modes are termed direct short-range routes of pathogen transmission, both requiring the close proximity of individuals, while the third is an indirect long-range route of transmission. Violent expirations release multiphase turbulent flows that are generally composed of buoyant hot moist air and suspended droplets of various sizes. These droplets contain components such as pathogens and minerals that can form droplet nuclei after evaporation of the drop's liquid phase. At low Reynolds number, the Stokes settling speed $U_s = gd^2/(18\mu)(\rho_d - \rho)$ of a droplet of diameter d and density $\rho_d$ in an ambient gas phase of density p is proportional to its surface area which necessarily decreases with time due to evaporation. As a result, such ejecta can remain airborne and viable far longer than previously believed.

Given the high airborne viral load that exists in congested public spaces, it would seem natural to seek out such spaces to place a viral air sampler. The goal of such a sampler would be to sample trace species indicative of viral agents, concentrate such species to a level of at least 200 nano grams or better, and subject the viral species to continuous genomic sequencing. The viral concentration and sequence data ideally could then be uploaded to the 'cloud', for deterministic computer modeling that merges the data with other variables previously described, such as PAHO, weather, and social media input variables. The added advantage of the sequencing functionality is that emergent strains can be revealed in an almost near real-time fashion even before a patient-vector becomes symptomatic. An added benefit is that many patients who are symptomatic may never seek professional medical attention, and thus never end up as a PAHO data point. A distribution of automated viral air samplers worldwide, seeded in locations such as airports and train stations, could provide data never previously attainable in epidemiology.

Air Sampling for Pathogens

The proposed system is comprised of several key parts necessary to sample ambient air laden with target pathogens. The entrance to the air sampler utilizes a common aerosol impaction filtration method. High velocity air is channeled around a 90-degree bend, causing heavier fractions to impact and embed in the end channel. Soft media such as low vapor pressure grease allow heavy fraction to be permanently entrained. As lighter fractions negotiate the change in direction, subsequently smaller and smaller fractions can be derived through the stratification based on mass through the airflow. At a suitable point downstream, a cross current electrospray source is employed to nondestructively capture bioaerosols from the air flow, and remove them from the air stream via electrostatic forces. To employ electrostatic separation, the bioaerosols are nondestructively ionized using a process known as 'electrospray'. Electrospray is a the process by which a conductive fluid, in this case an aqueous solution, is utilized to produce a nanospray of desorbing droplets which attract and capture polar or polarizable species from the air, of which virions are a part. (The ability to non-destructively ionize a virus has been well reported in the literature, where electrospray air capture of polar and polarizable species was accidentally discovered by Fenn et al at Yale in 1984, where the author was a research student. Fenn was awarded the 2002 Nobel Prize in Chemistry for Electrospray mass Spectroscopy). As a charged species, final filtration is accomplished using an electrostatic filter, similar to those found on magnetic sector mass spectrometers. Preliminary identification and separation of the virion or biospecies can be achieved preferably using charge-detection mass spectrometry. In one embodiment of the disclosed invention, the electrospray consisting of an aqueous fluid, preferably a 50-50 water ethanol mix with preferably 1% NaCl, capturing ambient droplets containing pathogens such as viruses and/or bacteria, or discrete pathogen particles, the deposition of the pathogens onto a counter electrode witness plate is performed. A difference of potential between the electrospray source and the counter electrode witness plate, sufficient to produce a Taylor cone which thus produces an electrospray of charged droplets, attracts and captures ambient polar molecules and airborne liquid phase droplets which may contain pathogens, and deposits the droplets containing pathogens or discrete pathogens onto a 'witness plate'. Standard optical microscopy, obvious to those skilled in the art, may now be performed. Images of pathogens contained in the collected airborne media may then be examined using the neural network image analysis approach disclosed in this patent. Alternatively, the electrospray fluid may consist of an ionic liquid miscible with an aqueous fluid, preferably 1-butyl-3-methylimidazolium tetrafluoroborate, may be used to collect ambient pathogens and droplets that contain pathogens. Ionic liquids are room temperature salts with essentially zero vapor pressure. Owing to the high electrical conductivity of ionic liquids coupled with the low volatility, allows for immediate electron microscopy of the witness plate sample suitable for subsequent neural network image analysis.

In one embodiment of the disclosed invention, once virions have been selected, they are accumulated on an internal witness plate, in preparation for automated sequencing. The sequencer of choice is a nano-pore- device, The nanopore system produced by Oxford Nanopore, employs a bespoke, employing proprietary pore-forming proteins to create pores in membranes. Pore-forming proteins are common in nature. For example, the protein a-hemolysin and similar protein pores are found naturally in cell membranes, where they act as channels for ions or molecules to be transported in and out of cells. A protein nanoporea-hemolysin is a heptameric protein pore with an inner diameter of 1 nm, about 100,000 times smaller than that of a human hair. This diameter is the same scale as many single molecules, including DNA. In a nanopore DNA sequencing, the system may process the sample until a minimum of tenfold read coverage over specified regions of interest has been seen, until a specific mutation has been observed in a sample or until enough sequence data has been collected to reliably assemble a sample against a reference. As DNA/RNA moves through the pore, changes in electric potential are translated into genetic sequence data. After electrospray charging and sorting if incoming virions and subsequent lysing, the process then is concentrate, extract, genetic library prep, and continuous flow sequencing. Regardless of the genetic sequencer employed, the electrospray capture and pathogen selection concept is adaptable to any subsequent downstream analytical tool. The electrospray capture technology has been proven and applied to biowarfare agent capture under prior Navy, Marine Corps, and National Academy of Science support. In addition, the technology was featured in a NASA Tech Briefs edition in 2011 after application on a spacecraft air filtration system contract that included John Fenn and former astronaut Dr. Buzz Aldrin (NASA—Glenn Research Center, SBIR Phase II, Contract NNC08CA08C, Topic 06-2-X3.01-9427 GRC; J. Bango, Principal Investigator).

How Electrospray Air Capture Works

During World War I, John Zeleny did some experiments in which he passed a low flow of conducting liquid through a metal capillary tube or "needle" maintained at high potential relative to an opposing counter-electrode. The resulting intense field at the needle tip dispersed the emerging liquid into a fine spray of highly charged droplets. Zeleny also noted that as the droplets evaporated they became unstable and disrupted into a multiplicity of smaller droplets. Such instability had been predicted and characterized by Lord Rayleigh in 1883. He argued that evaporation of solvent would increase the surface charge density on the droplet until Coulomb repulsion would overcome the surface tension that held the droplet together. As the electrical potential between the source (needle or wick) is increased, the electrical attraction slowly overcomes the surface tension of the fluid and a cone is formed from which emerges a jet of fluid at the apex of that cone. This cone is called a "Taylor Cone" after Sir Geoffrey Taylor. This jet of fluid then breaks up into a plurality of droplets. The resulting "Rayleigh Instability" (like charges that repel one another) would disrupt the droplets into a multiplicity of yet smaller droplets.

In the early 1980's, John Fenn and his colleagues at Yale used this approach and added a counter-current bath gas of nitrogen, which forced the evaporation of the solvent, which contained the analyte-solute in the solvent of the spray. Repeated fissioning of the discrete droplets yields a single gas phase ion with multiple electrical charges. When introduced into a mass spectrometer, the masses of biomolecular proteins and even living intact viruses can be ascertained. Analytes must be a charged species or intact ion in order to be manipulated and detected by a mass analyzer. Prior to this, analytes typical of a biomedical nature would fragment or dissociate by other ionization methods. It is the revolutionary nature of electrospray that gave rise to the study of the field now known as "Proteomics" and where Fenn's contribution was recognized through the award of the Nobel Prize in Chemistry in 2002 mentioned earlier. Fenn reported for the first time intact ions of proteins and peptides and moreover, because of their multiple charges, the mass/charge ratios of those ions were greater than ever obtained in the past using any type of mass spectrometer.

It is appropriate to note the reasons for transforming neutral pathogens into charged ions before attempting characterization. They include (1) The ability to control the trajectories and destinations of charged species by appropriate combinations of electric and magnetic fields and (2) A detectability that is generally much greater for ions than for neutral species because each ion gives rise to at least one electron in a primary signal current that can be greatly amplified by well known techniques. Moreover, ion-electron multipliers can produce millions of electrons in signal current for each incident ion. It is also appropriate to comment on how sensitivity is best expressed, i.e. in what units? In chromatography, perhaps the most widely used of all analytical techniques, a specific quantity of analyte is injected into a flow of mobile phase entering a separation column. Sensitivity is thus defined in terms of the smallest amount of injected analyte, e.g. in pico-grams or pico-moles that will give rise to a distinguishable peak in the effluent. Sensitivity defined in this way is not very meaningful in applications where one wants to know the concentration of some species in a gas or liquid of interest or whether a particular species is present in that gas or liquid when the available quantity of that gas or liquid may be large relative the quantity required for the analytical procedure. In such cases the appropriate measure of sensitivity is the lowest concentration of analyte in a sample liquid or gas at which detection and identification can be achieved. This minimum detectable concentration is clearly a relevant measure of sensitivity in a search for, say, a toxic chemical species, by analyzing a stream of air from a region where they might be concealed. Unfortunately, much if not most of the available data on detection of explosives and chemical or biological warfare agents is reported in minimum detectable amounts rather than minimum detectable concentration. Results in terms of the former cannot be meaningfully translated into the units of the latter.

The inventor and his colleagues at Yale under John Fenn discovered that electrospray ionization, now traditionally used for mass spectrometry, has the ability to "getter" or capture polar or polarizable trace species from the air, of which bio-species are a part. Since 9/11, there has been a flurry of development of many new methods and devices to identify potentially toxic agents of all kinds. But what seems to be missing is the fact that one needs to capture enough of the target species in order to achieve detection. Dr. Fenn (2002 Nobel Prize Chemistry) one stated that the sensors should not be called detectors, but "identifiers", and that a "detector" is really composed of a collection device and an identifier. If we collect more analyte from the surrounding air-diluent, we need a less sensitive identifier and vice-versa. Even better if the collection device captures and concentrates only the class of materials of interest while ignoring the background. It should be mentioned that the process allows for non-destructive capture of all airborne pathogens, including spores, bacteria, and viruses out of the ambient air.

Charge Detection & Filtration of Specific Virions or Bacteria or Other Pathogens:

Electrospray has been demonstrated to non-destructively add charge to biological species, such as spores, bacteria, and viruses. Viruses that have been charged using electrospray have been shown to be capable of being coarsely separated from an air steam. So what do we do next to identify viruses that have been separated in an airstream? A way is needed to further filter virion particles, and concentrate them onto a surface for subsequent genetic sequencing.

For over three decades since John Fenn's discovery at Yale, electrospray ionization (ESI) has been used to ionize non-covalent complexes and subsequently transfer the intact ion into the gas phase for mass spectrometry (MS) analysis. ESI generates a distribution of multiple charged ions, resulting in a m/z spectrum comprised of a series of peaks, known as a charge state envelope. To obtain mass information, the number of charges for each peak must be deduced. For smaller biological analytes like peptides, the charge states are sufficiently resolved and this process is straightforward. For macromolecular complexes exceeding ~100 kDa, this process is complicated by the broadening and shifting of charge states due to incomplete desolvation, salt adduction, and inherent mass heterogeneity. As the analyte mass approaches the MegaDalton regime, the m/z spectrum is often comprised of a broad distribution of unresolved charge states. In such cases, mass determination is precluded. Charge Detection Mass Spectrometry (CDMS) is an emerging MS technique for determining the masses of heterogeneous, macromolecular complexes. In CDMS, the m/z and z of single ions are measured concurrently so that mass is easily calculated. With this approach, deconvolution of a m/z spectrum is unnecessary. This measurement is carried out by passing macroions through a conductive cylinder. The induced image charge on the cylindrical detector provides information about m/z and z: the m/z is related to its time-of-flight through the detector, and the z is related to the intensity of the image charge. As a result, given the megadalton masses of many viruses (Influenza average value was $174\times10^6$ daltons), the application of charge detection spectrometric techniques is appropriate to the present tasking.

As electrospray charged pathogens such as viruses are sampled away from the aerosol pre-filter, an image charge will be produced each time a virus particle passes through the flight tube, FIG. 3. Therefore, a viral count can be obtained (analogous to blood cell counts in a Coulter counter), in addition to m/z charge spectral information about the specific virion selected. Knowing the mass and the viral counts, the quantity of viral particles can be deduced as collected on the witness plate or analysis target inside the CDMS system. Deposition on the discharge or witness plate is the last step before introduction to the genetic sequencer, if the target is not the sequencer itself. Being charged species, an electrostatic gating system may be created where arriving viral particles can be alternately introduced into the genetic sequencer front end, or discharged and collected for subsequent study, or destroyed as desired.

It should be noted that inventive claims extend to charge detection spectrometry performed at or near atmospheric pressure. In addition, ion mobility may be substituted for charge detection spectrometry at or near atmospheric pressure for charged bio-species sorting subsequent to preferred nanopore identification.

Viral Lysis

Several lysis methods may be employed in the sampler. Traditional reagent-thermal based methods may be employed, or, a reagentless electrical lysis approach may be employed, which has been demonstrated for vaccinia virions. Using a pair of nano electrodes, an externally applied electric field produces the trans-membrane potential, and it generates electric field inside the lipid bilayer membrane. This internal electric field generates a Maxwell stress, compressing the membrane in the normal direction, and rupture the membrane if the electric field is above critical value. Electric lysis is virtually instantaneous, whereas traditional reagent based approaches require up to 30-45 minutes per sample.

One aspect of standard reagent lysis is the fact that the process is performed using aqueous fluids at atmospheric pressure. In ESI-MS and ESI-CDMS, the collected species will be subjected to a partial pressure region, where aqueous fluids would instantaneously evaporate. One solution to low pressure viral lysis, aside from the aforementioned electric field method, is the use of ionic liquids, which have recently been shown to not only lyse virion capsids, but do so in some cases at higher efficiency than commercial reagent kits. Ionic liquids are room temperature salts, which have essentially zero vapor pressure. In addition, ionic liquids may serve an added purpose in helping perform genetic sequencing, discussed in the section on improved nanopore sequencing.

Sequencing

Virions in the airstream, once ionized by electrospray, filtered and sequestered based on mass and charge information, are now ready for sequencing. As indicated earlier, the preferred sequencing device is a graphene nanopore system, although any sequencer could in theory be utilized. A graphene nanopore device deduces genetic sequences based on an ionic current through a set of nano sized voids or pores, and measures the changes in current as biological molecules pass through the pore or near it. The information about the change in current can be used to identify that molecule compared to a library. A nanopore can be thought of as a genetic Coulter counter, referring to the idea of blood cell counts through a capillary in the presence of a conductive electrolyte, coupled to a pico-ammeter to measure the pulses.

The most significant advantage of a nanopore system aside from its small size and speed, however, is the lack of need for PCR amplification, as only 200 ng or less of viral material is required for analysis. As a strand of DNA is passed through a nanopore, the current is changed as the bases G, A, T and C pass through the void in different combinations. In addition, the system is the ability to continuously sample material.

Graphene sheets are now being tested by several investigators, which improve both the resolution and speed in which nucleotide sequences can be sampled using nanopore technology. This will allow sampler reduced in size and higher sensitivity of the sequencer to incoming genomic samples.

Improved Nanopore Genetic Sequencing in Vacuo

Nanopore sequencing resolution can be improved by using graphene sheets in lieu of protein based nanopore structures. However, real-time DNA sequencing is currently a major challenge because longitudinal current detection cannot distinguish individual nucleotides due to the thickness of membrane (>10 bases) and the fast translocation of a single base[1]. In any nanopore system, an electrolyte is required to create an ion flow from one side of the pore to the other, dragging along the nucleotide strand with it. It is hereby proposed to use an ionic liquid as the electrolyte, or a silicone based diffusion pump oil seeded with an ionic liquid. The point of this approach is that the witness plate in the charge detection mass spectrometer can actually be the genetic sequencer in vacuo! In fact, it may be possible to create hundreds, if not thousands, of graphene nanopore sequencer 'cells', arranged in a matrix such that each cell can be selected for new genome sample processing depending on the desired type of virion being interrogated. The charged virions emitted from the charge detection mass spectrometric filter (we use the term charged particle as the virus is not an ion in the traditional sense), and electrostatically or magnetically deflected to the desired sequencing cell.

This concept can be envisioned as a charged species equivalent to the old style cathode ray tubes used in early televisions and computer monitors. In those devices, an electron beam was continually deflected and scanned across a phosphor-coated screen to complete a raster. Similarly, one can deflect charged virions to any desired target for immediate analysis or sequesterization for subsequent laboratory study.

Improved Nanopore Nucleic Acid Sequence Correlation

One issue with nanopore genetic sequencing is that the nucleic acid strand passes through the pore very quickly, such that the resulting charge fluctuation due to individual base pairs may not yield as sharp discrete steps as would be the case if the strand passed through the pore more slowly. This reduces current resolution and thus nucleic acid identification accuracy. At present, this is dealt with by repetitive scans that are averaged or correlated over time to produce the desired current change indicative of the target sequence. One possible solution to this problem is the use of alternating current or AC instead of a DC bias in the electrolyte solution across the nanopore. By varying the frequency, polarity, and duty cycle of the applied potential, the target strand can be repetitively moved back and forth through the nanopore, permitting the requisite iterative sweeps required for acceptable signal averaging in far less time than using DC.

Reference Numerals:

FIG. 1:

10 Represents a conductive fluid capable of electrospray operation which may be volatile or non-volatile 20 Denotes a needle or tube or capillary for containing and supporting an electrospray
30 Is a Taylor Cone
40 Is a jet of fluid from an electrospray
50 is a dispersion of electrospray droplets
60 represents the coulomb explosion of electrospray droplets
70 represents desorbing electrospray droplets
80 represents bio-aerosol species in air being attracted to desorbing electrospray droplets
90 is a collection plate or witness plate for collection of charged bio species
100 is a collection plate or surface that is preferably a nanopore target
110 represents a power supply providing an electrical potential sufficient to yield a Taylor Cone from a needle or capillary 20 or paperspray source FIG. 2:
40 represents an electrospray source in totality encompassing elements 20,30,40, and 110 from FIG. 1
80 represents incoming ambient bioaerosols just before contact with electrospray droplets as in reference 80
120 is a capillary tube
130 are skimmers used to streamline the incoming charged species into a singular beam or linear stream of charged species
140 is an image charge detector tube
150 is a collection plate or target
160 is a picoammeter coupled to analysis device such as a computer FIG. 3:
170 Is a power supply for creating a difference of potential on either side of a nanopore 180 represents a strand of DNA, RNA, or any nucleotide sequence, or a protein or other biological molecule
190 is a nanopore, preferably in a sheet of graphene
200 is an electrolyte solution FIG. 4:
180 represents a strand of DNA, RNA, or any nucleotide sequence, or a protein or other biological molecule
200 is an electrolyte solution FIG. 5:
210 is a diagram of a cathode ray tube
220 is a diagram of a charged particle delivery system
230 is the sample inlet
240 is an electrospray source
250 is an electrostatic focusing system for the electrospray
260 represents horizontal electrostatic deflection plates
270 represents vertical electrostatic deflection plates
280 represents a nanopore detection target
290 represents a beam of charged bio-species, such as organic ions, viruses, bacteria, prion, protein, or nucleic acid FIG. 6:
300 Denotes the starting point of one scan preferred raster scanning of charged bio-species into well targets for preferred nanopore analysis
310 Denotes the end point of one scan preferred raster scanning of charged bio-species into well targets for preferred nanopore analysis FIG. 7:
320 Denotes ambient air laden with bio-aerosol species sample introduction
330 Denotes 1$^{st}$ stage heavy fraction filtration
340 Denotes electrospray charging of ambient bio aerosol species
350 Denotes second stage electrostatic filtration of bio species
360 Denotes charge detection mass spectroscopy and gating electrodes
370 Denotes lysing, extraction, and nanopore sequencing
380 Denotes data extraction step
390 Denotes Data transmission or migration to data cloud, internet, or network
400 Denotes application of predictive modeling algorithm Detailed Description of Drawings FIG. 1 is a diagram of the electrospray capture process for biological trace species from the air. The process begins with the introduction of a conductive fluid driven by either capillary action or hydrostatic force into an electrically conductive needle 20, where a difference of electric potential is applied between the needle 20 and a target 90 using a power supply 110 capable of creating a Taylor Cone 30 from which emerges a jet of fluid 40 which as the fluid evaporates 50, results in desorbing droplets 70, said droplets carrying a surface charge such that ambient biological species 80 are attracted and absorbed by aforementioned desorbing droplets 60, until only charged biological trace species remain and are deposited onto the opposing electrical pole target 90, which is preferably a graphene nanopore with an electrolyte on either face, said electrolyte preferably being a low volatility ionic liquid that will not evaporate under any level of vacuum, to which a difference of electrical potential has been applied.

FIG. 2 illustrates the preferred embodiment of the invention, a charge detection mass spectrometer with a target that consists of a nanopore detector 150. The electrospray source 40 emits desorbing electrospray droplets to which ambient polar or polarizable biological trace species in the air are attracted 80 and absorbed by the droplets, resulting in discrete charged particles. The charged biological particles pass through a capillary tube 120 and into a succession of progressively pumped regions separated by skimmers 130 and through an image charge detector tube 140, said image charge of charged biological trace species being detected and amplified by a picoammeter and computer 160, before encountering end target 150 that is preferably a nanopore device capable of both lysing biological trace species and allowing a charge fluctuation of nucleic acid or other biological molecular group to pass through said nanopore, allowing identification of each molecular or atomic group or species.

FIG. 3 discloses a nanopore nucleotide detection configuration. The nanopore, preferably a nano scale hole through a graphene sheet 190, where an electrolyte 200 is in contact with on either side, whereby a difference of potential 170 has been applied, such that a biological molecule, preferably a nucleotide sequence such as DNA 180, can be driven by ionic flow and pass through the aforementioned nanopore 190.

Figure 4:
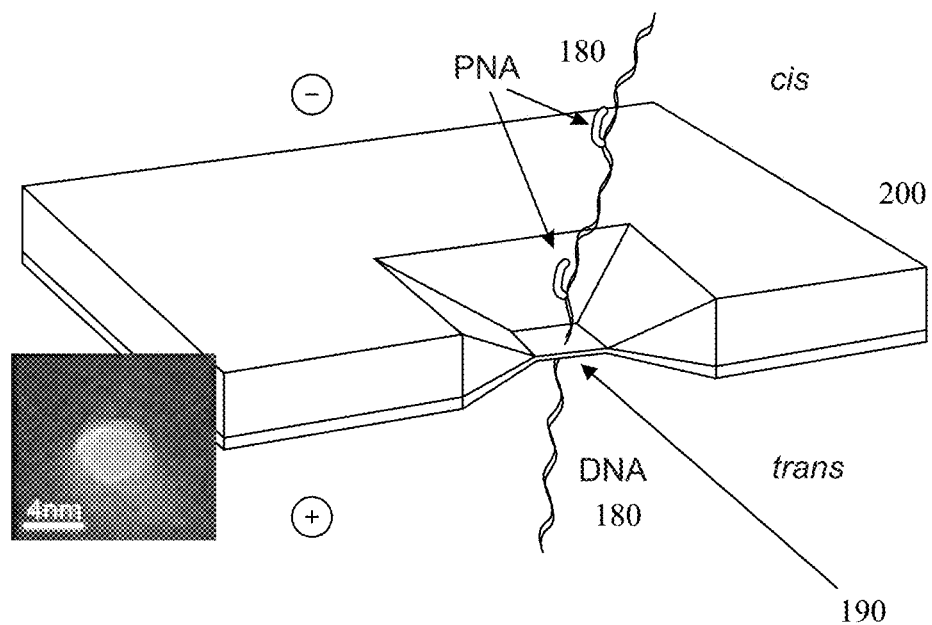
FIG. 4 is a close-up drawing of a graphene nanopore.

FIG. 4 is a close up picture of a graphene nanopore 190 where a nucleotide sequence such as DNA 180 can pass through said nanopore 190, so driven by the flow of ions in an electrolyte solution in contact with both sides of the graphene sheet, insulated by a dielectric 200 from both sides of the nanopore.

FIG. 5 is of two devices, a charged particle delivery system 220, and a cathode ray tube or CRT 210, upon which it is based. In a CRT, an electron gun emits electrons from a heated filament, which are electrostatically focused and then deflected using electrostatic or electromagnetic means such that a scan of the phosphor coated screen can be scanned in a successive raster pattern. The phosphor screen illuminates in the visible spectrum when high energy electrons strike its surface.

In the preferred charged particle delivery system 220, electrospray charged bioaerosol trace species 230, devoid of solvent or aqueous solution and introduced into a preferably partial pressure region, passing through a charge detection mass spectrometer tube 240, are electrostatically focused 250, and then deflected by horizontal 260 and vertical 270 plates, and scanned in a raster pattern or simply directed to a specific target on a nanopore detection surface 280, said charged bio-aerosol consisting of particulates or virions or nucleic acid or bacteria, or protein or peptide or any bio-species 290.

Figure 6:
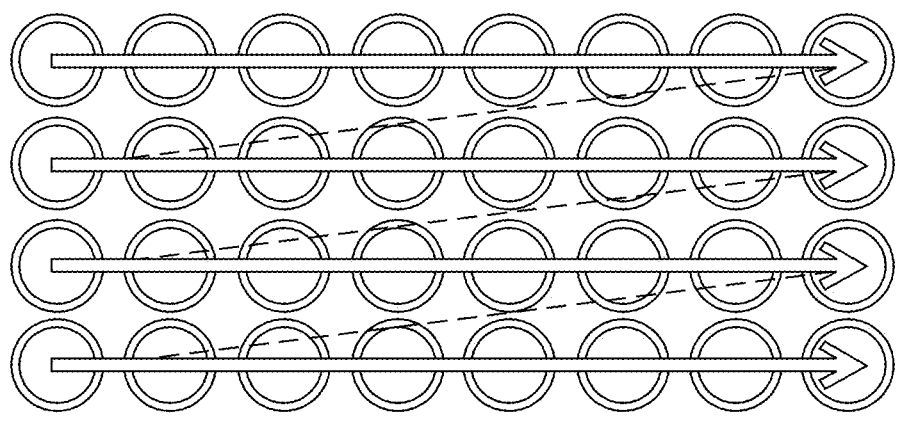
FIG. 6 is a drawing of a raster pattern.

FIG. 6 is a raster pattern with a beginning point 300 and a terminal point 310, before the scan is retraced to the next level below or down next to and parallel to the preceding row of scan targets. Each target preferably represents an individual graphene ionic liquid nanopore well. Successive wells permit selective analysis depending upon the composition of the charge detection bio-particulate sample.

Figure 7:
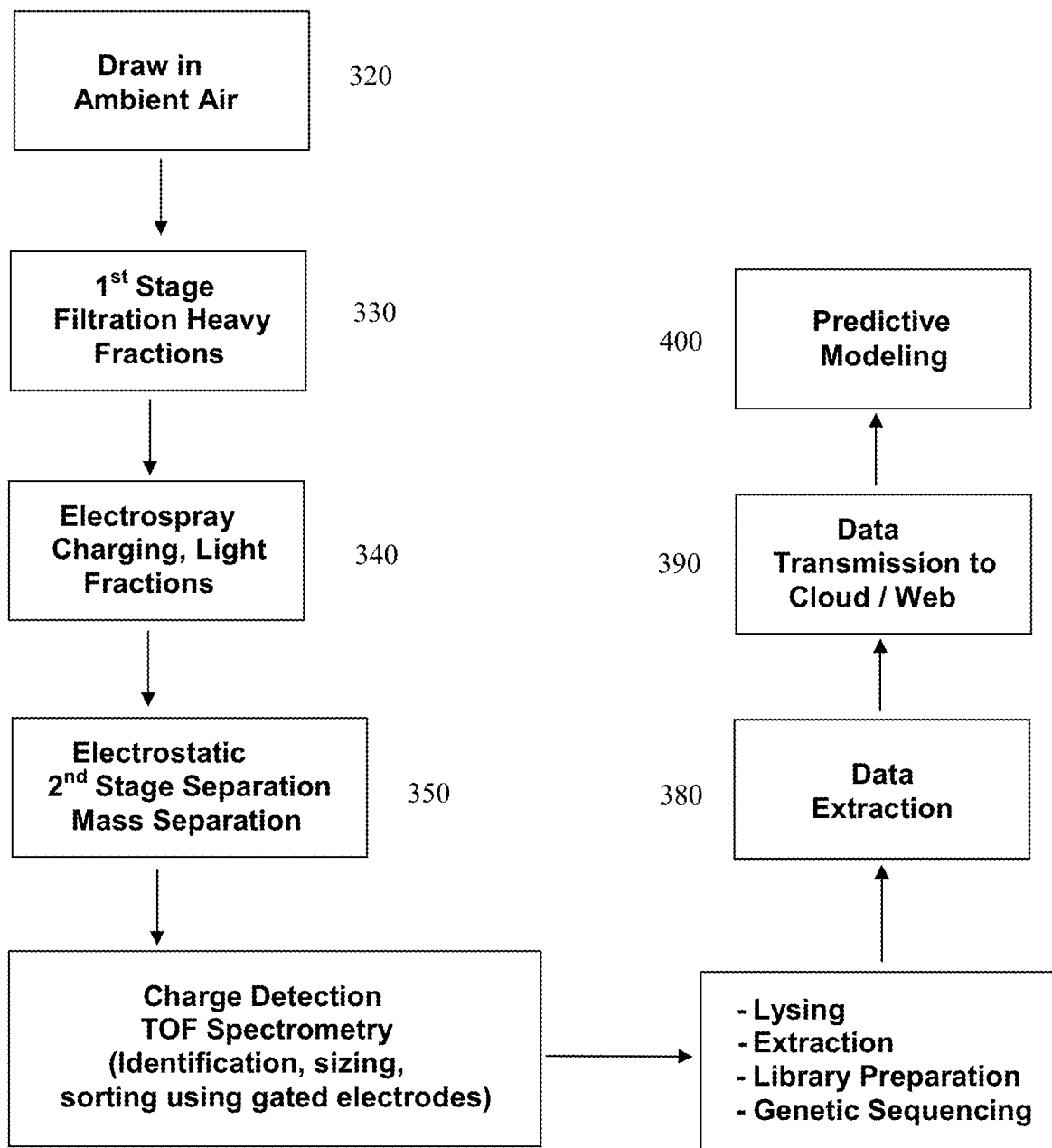
FIG. 7 is a flowchart of a bio-aerosol and infectious agent air sampling method.

FIG. 7 is a flowchart of the preferred bio-aerosol and infectious agent air sampling system. Ambient air containing bio-species 320 is drawn in using a fan or other fluid movement device, where heavy fractions 330 are separated using aerosol separation techniques such as moving through a sharp bend. The bioaerosols are electrically charged after undergoing interactions with an electrospray plume 340. Electrostatic separation 350 further refines the charged particulates, Charge detection mass spectrometry provides charged bio-aerosol or pathogen image charge and m/z value, after which lysing, nucleic acid extraction, and genetic sequencing is performed 370, after which the fusion of data analysis and extraction 380 is performed, whereby said data is uploaded to the internet or cloud or other network 390, for subsequent predictive modeling 400.

Below are some embodiments of the disclosed surveilling and forecasting devices and air sampling methods.

Embodiment 1. A device to surveil and forecast public health and force protection pathogen threats, including viral outbreaks, the device comprising: (a) an air sampler utilizing aerosol impaction filtration, causing heavier fractions to impact and embed in an end channel, lighter fractions negotiating the change in direction, subsequently lighter fractions can be derived through a stratification based on mass through an airflow; (b) a cross current or counter current electrospray source employed to nondestructively capture bioaerosols from the air flow, and remove them from the air flow via electrostatic forces; (c) filtration accomplished using an electrostatic filter, preliminary identification and separation of a virion or a biospecies achieved using a charge detection mass spectrometer; (d) bioaerosols accumulated on a witness plate, in preparation for automated sequencing in a sequencer, the sequencer being a nanopore device, and the sequencer outputting a genetic sequence; (e) electrospray charged pathogens sampled away from an aerosol pre-filter, an image charge produced each time a pathogen particle passes through a flight tube, a viral or bacterial count obtained in addition to m/z charge spectral information about a specific pathogen or virion selected; (f) an ionic liquid acting as an electrolyte in nanopore sequencer, or a silicone based diffusion pump oil seeded with an ionic liquid; and wherein the device is configured to perform a low pressure viral lysis via ionic liquids.

Embodiment 2. The device of embodiment 1, wherein the charge detection mass spectrometer comprises: desorbing electrospray droplets to which ambient polar or polarizable biological trace species in the air are attracted, and absorbed by the droplets, resulting in discrete charged particles, a capillary tube configured to receive and pass through the charged biological particles into a succession of progressively pumped regions separated by skimmers and through an image charge detector tube; a picoammeter and computer configured to detect and amplify the image charge of charged biological trace species; a target that consists of a nanopore sequencer, the target configured to both lyse biological trace species and allow a charge fluctuation of nucleic acid or other biological molecular group to pass through the nanopore detector thereby identifying each molecular or atomic group or species thereof.

Embodiment 3. The device of embodiment 2, wherein the trace species are electrospray charged bioaerosol trace species, devoid of solvent or aqueous solution, and introduced into a preferably partial pressure region, passing through a charge detection mass spectrometer tube, electrostatically focused, deflected by horizontal and vertical plates, scanned in a raster pattern or simply directed to a specific target on a nanopore detection surface, said charged bioaerosol trace species consisting of particulates or virions or nucleic acid or bacteria, or protein or peptide or any bio-species.

Embodiment 4. The device of embodiment 3, wherein the charge detection mass spectrometer tube, and horizontal and vertical plates, are configured to scan the scanned in raster pattern in a successive raster pattern with a beginning point and a terminal point, before the raster pattern is retraced to the next level below or down next to and parallel to a preceding row of scan targets, each target represents an individual ionic liquid nanopore well, and successive wells permit selective analysis depending upon the composition of the electrospray charged bioaerosol trace species.

Embodiment 5. A bioaerosol trace species air sampling method, the method comprising: sampling ambient air containing bioaerosol trace species drawn in using a fan or other fluid movement device; separating heavy fractions using aerosol separation techniques; interacting the bioaerosol trace species with an electrospray plume to electrically charge the bioaerosol trace species; refining the charged bioaerosol trace species using electrostatic separation; performing a charge detection mass spectrometry on the bioaerosol trace species; providing charged bioaerosol trace species image charge and m/z value; lysing the bioaerosol trace species; extracting nucleic acid from the bioaerosol trace species; performing genetic sequencing on the bioaerosol trace species; performing fusion of data analysis and extraction; uploading data from the performing fusion of data analysis and extraction act to a network for subsequent predictive modeling.

Embodiment 6. The device embodiment 1, further comprising a low vapor pressure grease located in the air sampler utilizing aerosol impaction filtration and configured to allow heavy fraction to be permanently entrained.

Embodiment 7. The device of embodiment 2, further comprising: conductive fluid driven by either capillary action or hydrostatic force into an electrically conductive needle, where a difference of electric potential is applied between the needle and the target using a power supply configured to create a Taylor Cone from which emerges a jet of fluid which as the fluid evaporates, results in desorbing droplets, said droplets carrying a surface charge such that ambient biological species are attracted and absorbed by aforementioned desorbing droplets, until only charged biological trace species remain and are deposited onto an opposing electrical pole target, which is a nanopore with an electrolyte on either face, said electrolyte preferably being a low volatility ionic liquid that will not evaporate, to which a difference of electrical potential has been applied.

Embodiment 8. The device of embodiment 1, wherein the charge detection mass spectrometer is configured to operate at or near atmospheric pressure.

Embodiment 9. The device of embodiment 1 where an ion mobility spectrometer is substituted for the charge mass spectrometer at or near atmospheric pressure for charged bio-species sorting subsequent to preferred nanopore identification.

Embodiment 10. The device of embodiment 1 further comprising: an electrostatic gating system where arriving pathogen particles can be alternately introduced into the genetic sequencer, or discharged and collected for subsequent study, or destroyed as desired.

Embodiment 11. The device of embodiment 1, further comprising: nanopore sequencer cells, arranged in a matrix such that each cell can be selected for new genome sample processing depending on the desired type of virion being interrogated, and wherein the charged virions emitted from the charge detection mass spectrometer and the charged virions are electrostatically or magnetically deflected to a desired sequencing cell.

Embodiment 12. The method of embodiment 5, wherein the aerosol separation technique is moving the bioaerosol trace species through a sharp bend.

Embodiment 13. The method of embodiment 5, wherein the network is an internet or cloud computing network.

Embodiment 14. The device of embodiment 1, further comprising: distributed air samplers using electrospray pathogen capture introduced into a partial pressure region for charge detection mass spectrometry.

Embodiment 15. The device of embodiment 1, furthering comprising electrostatic fields configured to separate bacteria from viruses.

Embodiment 16. The device of embodiment 1, wherein the sequencer is coated with a non-volatile electrolyte.

Embodiment 17. The device of embodiment 1, wherein the sequencer is configured to upload the genetic sequence to a cloud computing network.

Embodiment 18. The device of embodiment 1, wherein the sequencer is configured to perform a comparative analysis of the genetic sequence a genetic sequence stored in a database.

Embodiment 19. A method for analysis of pathogens, the method comprising:

seeding areas of human congestion with distributed air samplers; continuously drawing air into the distributed air samplers; filtering out larger fractions from the air until only specific bioaerosols are left; electrospraying the bioaerosols such that the bioaerosols become charged ions; applying a combination of electrostatic filtration and charge detection spectrometry to the charged ions so that target pathogens are accumulated; performing genetic sequencing on the target pathogens via a genetic nanopore analyzer such that a nucleotide sequence data is produced; uploading the genetic sequence data to a cloud computing network; and predicting the outbreak of pathogen strains based on the analysis of the genetic sequence data by the cloud computing network.

Embodiment 20. A charge detection mass spectrometer comprising: a nanopore detector; an electrospray source in communication with the nanopore detector, the electrospray source configured to emit desorbing electrospray droplets to which ambient polar or polarizable biological trace species in the air are attracted and absorbed by the droplets, resulting in discrete charged biological particles; a capillary tube configured to pass through the charged biological particles; a succession of progressively pumped regions separated by skimmers in communication with the capillary tube, and configured to pass through the charged biological particles; an image charge detector tube in communication with the success of progressively pumped regions, the image charge detector tube configured to produce an image charge of the charged biological particles; a picoammeter and a computer configured to detect and amply the image charge; and the nanopore detector configured to lyse and allow the lysed biological particles to pass through a nanopore, and wherein the charge detection mass spectrometer can identify the lysed biological particles.

Embodiment 21. A method of sampling air for bioaerosols and pathogens, the method comprising: drawing air into a system using a fluid moving device; separating heavy non-biological fractions using aerosol separation techniques and producing bioaerosols; interacting the bioaerosols with an electrospray plume to create charged bioaerosols; performing electrostatic separation on the charged bioaerosols; performing charge detection mass spectrometry on the charged bioaerosols to produce pathogen image charges and m/z values; lysing the charged bioaerosols; extracting nucleic acid from the charged bioaerosols; performing genetic sequencing on the charged bioaerosols; performing data analysis and extraction on data derived from the steps above; uploading the data, data analysis, and extraction to a cloud computing network for predictive modeling.

Embodiment 22. A system to surveil and forecast public health and force protection pathogen threats, including viral outbreaks, the system comprising: a first device comprising: (a) an air sampler utilizing aerosol impaction filtration, causing heavier fractions to impact and embed in an end channel, lighter fractions negotiating the change in direction, subsequently lighter fractions can be derived through a stratification based on mass through an airflow; (b) a cross current or counter current electrospray source employed to nondestructively capture bioaerosols from the air flow, and remove them from the air flow via electrostatic forces; (c) filtration accomplished using an electrostatic filter, preliminary identification and separation of the virion or biospecies achieved using an ion mobility spectrometer; (d) bioaerosols accumulated on a witness plate, in preparation for automated sequencing in a sequencer, the sequencer being a nanopore device, and the sequencer outputting a genetic sequence; (e) electrospray charged pathogens sampled away from an aerosol pre-filter, an image charge produced each time a pathogen particle passes through a flight tube, a viral or bacterial count obtained in addition to m/z charge spectral information about a specific pathogen or virion selected; (f) an ionic liquid configured as an electrolyte in nanopore sequencer, or a silicone based diffusion pump oil seeded with an ionic liquid; (g) low pressure viral lysis via the ionic liquid; a second device located away from the first device, the second device comprising: (a) an air sampler utilizing aerosol impaction filtration, causing heavier fractions to impact and embed in an end channel, lighter fractions negotiating the change in direction, subsequently lighter fractions can be derived through a stratification based on mass through an airflow; (b) a cross current or counter current electrospray source employed to nondestructively capture bioaerosols from the air flow, and remove them from the air flow via electrostatic forces; (c) filtration accomplished using an electrostatic filter, preliminary identification and separation of the virion or biospecies achieved using an ion mobility spectrometer; (d) bioaerosols accumulated on a witness plate, in preparation for automated sequencing in a sequencer, the sequencer being a nanopore device, and the sequencer outputting a genetic sequence; (e) electrospray charged pathogens sampled away from an aerosol pre-filter, an image charge produced each time a pathogen particle passes through a flight tube, a viral or bacterial count obtained in addition to m/z charge spectral information about a specific pathogen or virion selected (f) an ionic liquid configured as an electrolyte in nanopore sequencer, or a silicone based diffusion pump oil seeded with an ionic liquid; and (g) low pressure viral lysis via the ionic liquid; a third device located away from the first device and second device, the third device comprising: (a) an air sampler utilizing aerosol impaction filtration, causing heavier fractions to impact and embed in an end channel, lighter fractions negotiating the change in direction, subsequently lighter fractions can be derived through a stratification based on mass through an airflow; (b) a cross current or counter current electrospray source employed to nondestructively capture bioaerosols from the air flow, and remove them from the air flow via electrostatic forces; (c) filtration accomplished using an electrostatic filter, preliminary identification and separation of the virion or biospecies achieved using an ion mobility spectrometer; (d) bioaerosols accumulated on a witness plate, in preparation for automated sequencing in a sequencer, the sequencer being a nanopore device, and the sequencer outputting a genetic sequence; (e) electrospray charged pathogens sampled away from an aerosol pre-filter, an image charge produced each time a pathogen particle passes through a flight tube, a viral or bacterial count obtained in addition to m/z charge spectral information about a specific pathogen or virion selected; (f) an ionic liquid configured as an electrolyte in nanopore sequencer, or a silicone based diffusion pump oil seeded with an ionic liquid; and (g) low pressure viral lysis via the ionic liquid.

Embodiment 23. The device of embodiment 16, wherein the non-volatile electrolyte is ionic liquid.

Trained human microbiologists are very good at deducing what a micro organism is based on many physical characteristics such as the size, shape, surface factors, attachments, and motility of a bacteria for example. While physical characteristics alone may not positively identify an specific organism, the physical attributes can help truncate the list of possibilities to a small handful, where other factors such as optical light adsorption and chemical markers can finalize the identification.

In order for an artificial intelligence or AI system to become effective, the software must learn by experience, using examples that are guided by outside intervention to help the code evolve into a better processor of input visual machine vision. The disclosed patent reveals a way whereby a new software tool that builds on the CAPTCHA system that uses human interaction to define certain elements in an unknown or known visual field, can assist in improving machine vision AI code. By fielding the software of a Biological CAPTCHA or b-CAPTCHA to millions of human users worldwide, AI software can undergo deep learning far faster than without such evolutionary software modifications.

The COVID-19 pandemic has exemplified the need for better and faster means for identification of new and emerging infectious agents. In the clinical laboratory, virtually all procedures have been automated save for the actual identification of bacterial and viral agents. The disclosed study addresses this need, and proposes a possible solution based on deep machine learning and CAPTCHA principles to assist in artificial intelligence in support of improved automated infectious agent identification.

The complexities inherent in the wide variety of morphological variations in infectious agents makes the determination of type and class of agent extremely challenging, necessitating trained human interface. Borrowing from techniques used in cyber security, machine learning is possible that can enhance the decision matrix. What does cyber security have to do with identification of bacteria by visual means? At first glance it might appear that the two have nothing to do with each other. Upon closer examination; however, the two are in fact related.

With the advent of present Internet linked computer platforms, there are those who wish to circumvent cyber security so they can take advantage of unsuspecting individuals. As anyone who has ever purchased concert tickets or signed up for an account on a website, they have undoubtedly encountered a challenge response test known as a CAPTCHA. The CAPTCHA is an image that displays two distorted words or numbers. The goal of the CAPTCHA is to allow the website to verify that the information being entered is being entered by a human and not a computer or "bot".

The term CAPTCHA is an acronym that means—Completely Automated Public Turing test to tell Computers and Humans Apart.

There have been people who utilize computers to buy up large blocks of concert or theater tickets, only to later resell them at a higher price. Hackers have used computers or bots to log onto e-mail servers to create many fake e-mail accounts that would later be used to create fake Facebook, Twitter, or Instagram accounts and also to stop spam. To thwart such website attacks by bots, CAPTCHA has been devised to help distinguish between a real person and an automated bot.

The late mathematician and computer scientist Alan Turing often mused about computers someday becoming sufficiently intelligent where they might be able to fool humans into thinking that a computer is actually a human. In one thought experiment, Alan Turing supposed an "imitation game" played by three people, a man (A), a woman (B) and an interrogator (C) who may be of either sex. The interrogator is located in a room apart from the other two were communication through a series of typewritten questions is permitted so as not to give away information related to the persons gender and has to determine the gender of each person.

Turing supposed that if a sufficiently well programmed computer takes the place of either "A" or "B", it would be difficult, if not impossible for the interrogator to deduce their gender. The theory behind the CAPTCHA is that humans are very good at discerning patterns and optical character recognition while contemporary computers are not as good as humans. If the website showed two known words that are visually distorted, a human would have a much easier time deciphering what the word is than would a computer, or more specifically, an optical character recognition (OCR) program.

Figure 8:
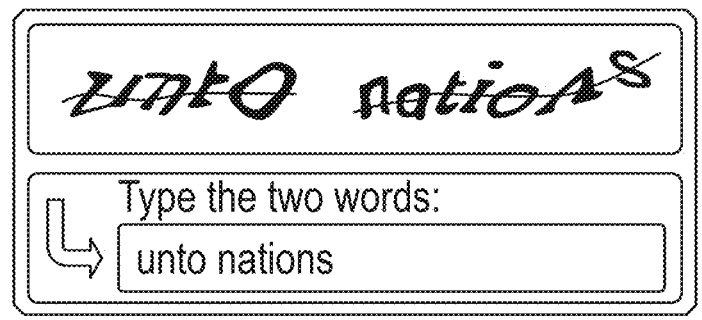
FIG. 8 is a drawing of a CAPTCHA icon.

FIG. 8 shows the older CAPTCHA icon that would be encountered on a website. The CAPTCHA shows two known words that are purposely distorted to make it hard for a computer or bot to decipher the words, but is relatively easy for a human.

In the previous CAPTCHA, the two distorted words that must be typed into the textbox are "unto" and "nations". Once the two correct words have been identified and typed into the text box, the website will allow access to the user because the probability of the user being a bot is extremely low.

After the success of CAPTCHA, it was decided that due to the enormous number of websites throughout the world utilizing CAPTCHA's, a secondary use can be realized. Instead of using two known words that have been purposely distorted, one known word will be randomly generated and purposely distorted and a second word or number (also purposely distorted) will be shown from an optical character recognition system that failed to discern the word or number. The significance of this is that there is an estimated 100 million CAPTCHA's utilized each day, so if the people solving the CAPTCHA could be put to work in decoding the word or number that an OCR program failed to recognize, the OCR program could be fine tuned to perform better. See FIG. 9.

Figure 9:
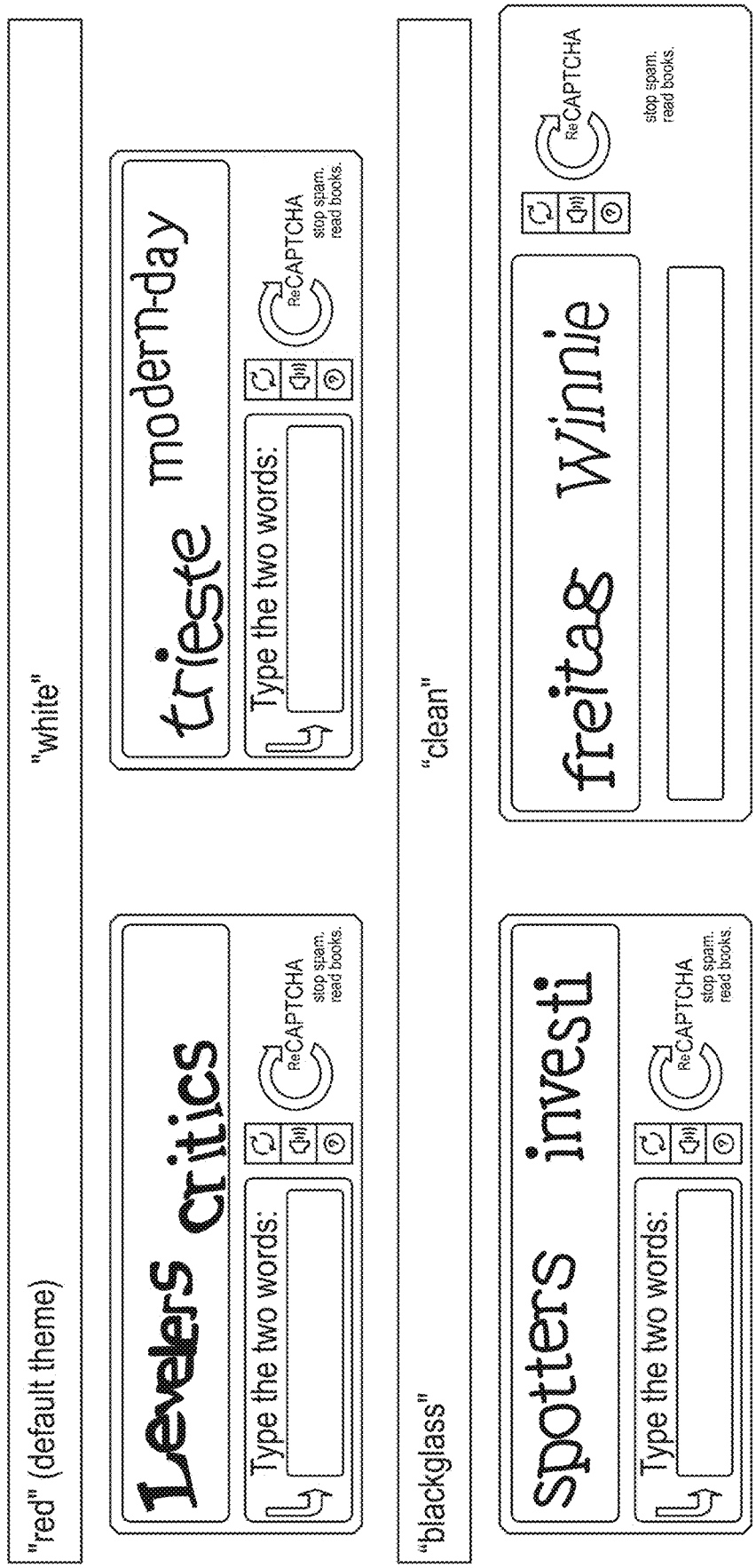
FIG. 9 is a drawing of four reCAPTCHA icons.

This next generation CAPTCHA is called reCAPTCHA, where a human is being unwittingly put to work determining what the correct word or number is that an optical character recognition system failed to identify. FIG. 9 is a set of four commonly encountered reCAPTCHA icons found on websites.

When an individual enters what they believe the two words are, one of the words is actually a known control word randomly generated by the website while the other word or number is the unknown that a previous OCR program failed to recognize. The order or the two words or numbers are randomly chosen by the website and both of the words or numbers are purposely distorted in a similar manner, so the user cannot simply guess at which is the control and which is the unknown. The reCAPTCHA relies on the fact that if the user can properly identify the purposely distorted known control word or number, then the probability is high that they can also decipher the purposely distorted unknown word or number. In this way, thousands of books and papers that were scanned using optical character recognition can benefit from the hundred million or so reCAPTCHA web users each day.

Because the purpose is to identify the unknown word or number, the reCAPTCHA servers will use the same unknown word or number several times. If the same response is reported from three separate users, the unknown word or number will be stored as a successfully identified word or number and will then be included into the control database. Some may ask, if the unknown word could not be identified by an OCR program, so why purposely distort it? The answer is so that the user will not be able to distinguish between the control word and the unknown word. In addition to identifying words or numbers that optical character programs have difficulty with, the reCAPTCHA can also be used to identify images or portions of images that contain specific visual information, such as specific shapes, specific colors, specific objects, etc.

Figure 12:
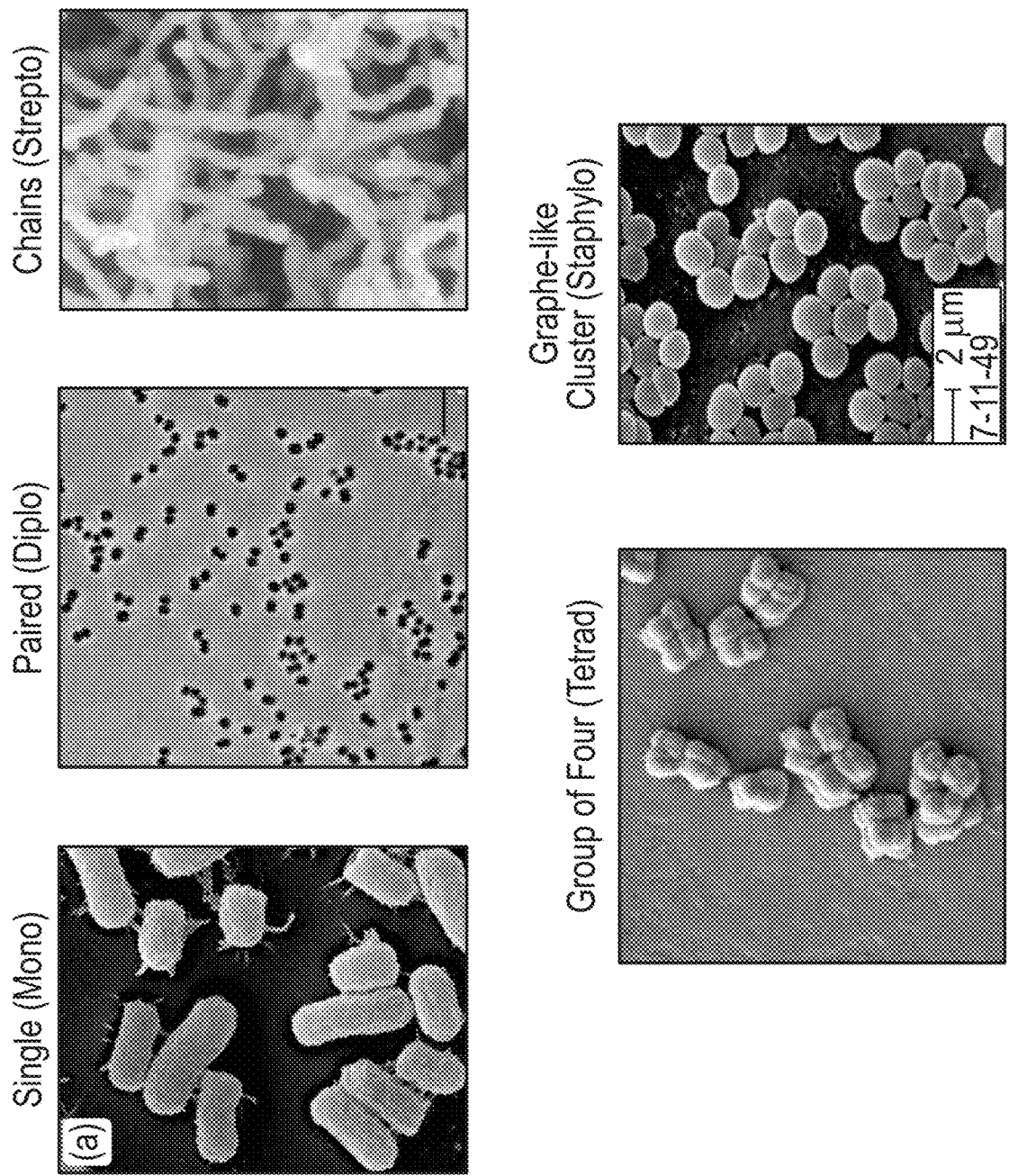
FIG. 12 is a drawing of 5 arrangements of bacteria.

FIG. 12 shows a reCAPTCHA. The reCAPTCHA in FIG. 12 shows nine different images of streets and sidewalks. The reCAPTCHA is setup to challenge the user to correctly identify all the images that contain fire hydrants.

When this information is saved, it could be used for refining an artificial intelligence programs ability to analyze images, or the newly marked images can be used in a future reCAPTCHA test.

The reCAPTCHA service is used to help digitize books, texts and other non-digital documents by enlisting humans to help identify words or numbers that OCR programs failed to identify. Companies such as Google (Google books project) and non-profits such as the Internet archive seek to preserve human knowledge in a digital form. After a paper document is photographically scanned and digitized, it is processed by optical character recognition software.

As good as OCR programs are, they are not perfect, so they cannot correctly identify 100% of the content. Some of the documents are aged and thus have yellowing pages and faded ink or wrinkles in the page or some other blemish or physical damage resulting from anywhere from as low as 1% to as much as 20% of the content unrecognized by the OCR program. Human transcribers are much more accurate than OCR programs, but are also much slower and much more expensive. The reCAPTCHA service puts everyone who has ever answered a reCAPTCHA to work by helping identify a word or number that an optical character recognition program failed to recognize. In the same way that Google has been using users to identify and categorize images with reCAPTCHA, we propose a similar biological reCAPTCHA that can be used to correctly identify pathogens in images based upon their morphology. Initially the biological reCAPTCHA will be used to correctly identify various pathogens and this information will be utilized by artificial intelligence (A.I.) to assist in the AI learning to identify unknown pathogens without user intervention.

The biological reCAPTCHA will be designated bCAPTCHA or b-CAPTCHA. biological Completely Automated Public Turing test to tell Characteristics and Heuristics Apart.

Figure 11:
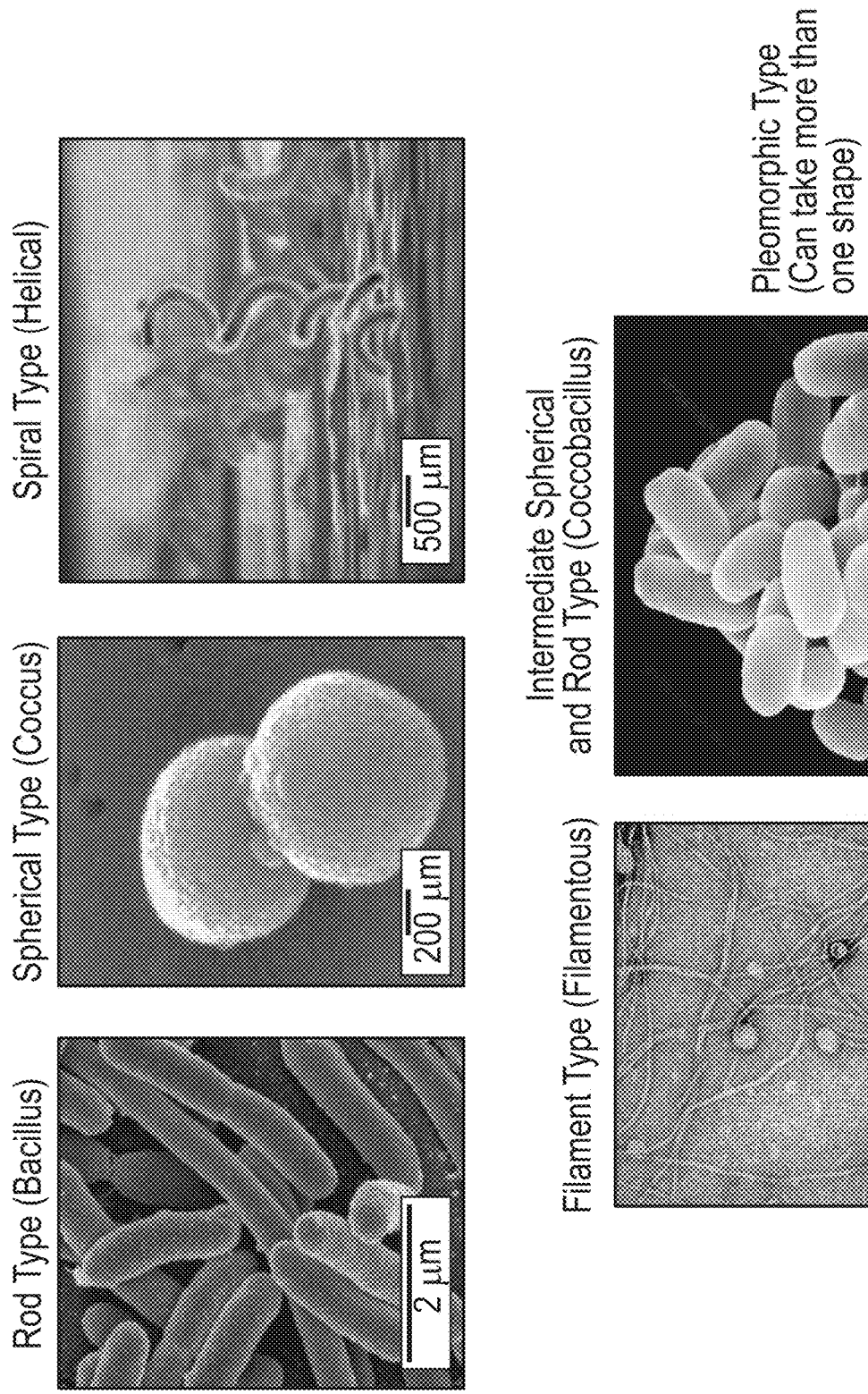
FIG. 11 is a drawing of four shapes for bacteria.

When bacteria are viewed under a sufficiently powerful microscope, they can be separated or grouped into several shapes. Although there are several different shapes of bacteria, the majority of bacteria fall into seven main shapes. FIG. 11 shows 5 types of shapes for bacteria: Rod type (bacillus) Source:https://opentextbc.ca/biology2eopenstax/chapter/structure-of-prokaryotes-bacteria-and-archaea /; Spherical type (coccus) Source:https://opentextbc.ca/biology2eopenstax/chapter/structure-of-prokaryotesbacteria-and-archaea /; Spiral type (helical) Source:https://opentextbc.ca/biology2eopenstax/chapter/structure-of-prokaryotes-bacteria-andarchaea /; Filament type (filamentous) Source: https://www.sciencephoto.com/media/874062/view/bordetella-pertussis-sem; Intermediate Spherical and Rod Type (Coccobacillus) Source:https://www.sciencephoto.com/media/874062/view/bordetella-pertussissem; Pleomorphic type (Can take more than one shape).

Along with the basic shapes, bacteria also have the additional aspect of arrangement, where the bacteria can be single, paired, clustered or in long chains. So far as the arrangement is concerned, it may be as shown in FIG. 12: Single (mono) Source: https://www.semanticscholar.org/paper/Fermentatio n-and-evaluation-of-Klebsiella-and-K.-on-Cho-Rathnasingh/9a1bc54993aee59434aa 3385af07ff6bb9befa31; Paired (diplo) Source: https://www.researchgate.net/figure/Effects-of-minC-knockout-onmorphology-of-N-gonorrhoeae-CSRC1-a-bphasecontrast_fig2_12168622; Chains (strepto) Source: https://www.britannica.com/science/Staphylococcus-aureus; Group of four (tetrad) Source: https://www.semanticschola-r.org/paper/Radiation-Resistant-Micrococcusluteus-SC1204-and-Deng-Yang/120e57c8ba62dd afdf3f92b1e274b293998e4e57; and Grape-like cluster (staphylo) Source: http ://biotracer.hugin.com/content/Biotracing_systems/foodmicro2008. pdf.

Figure 13:
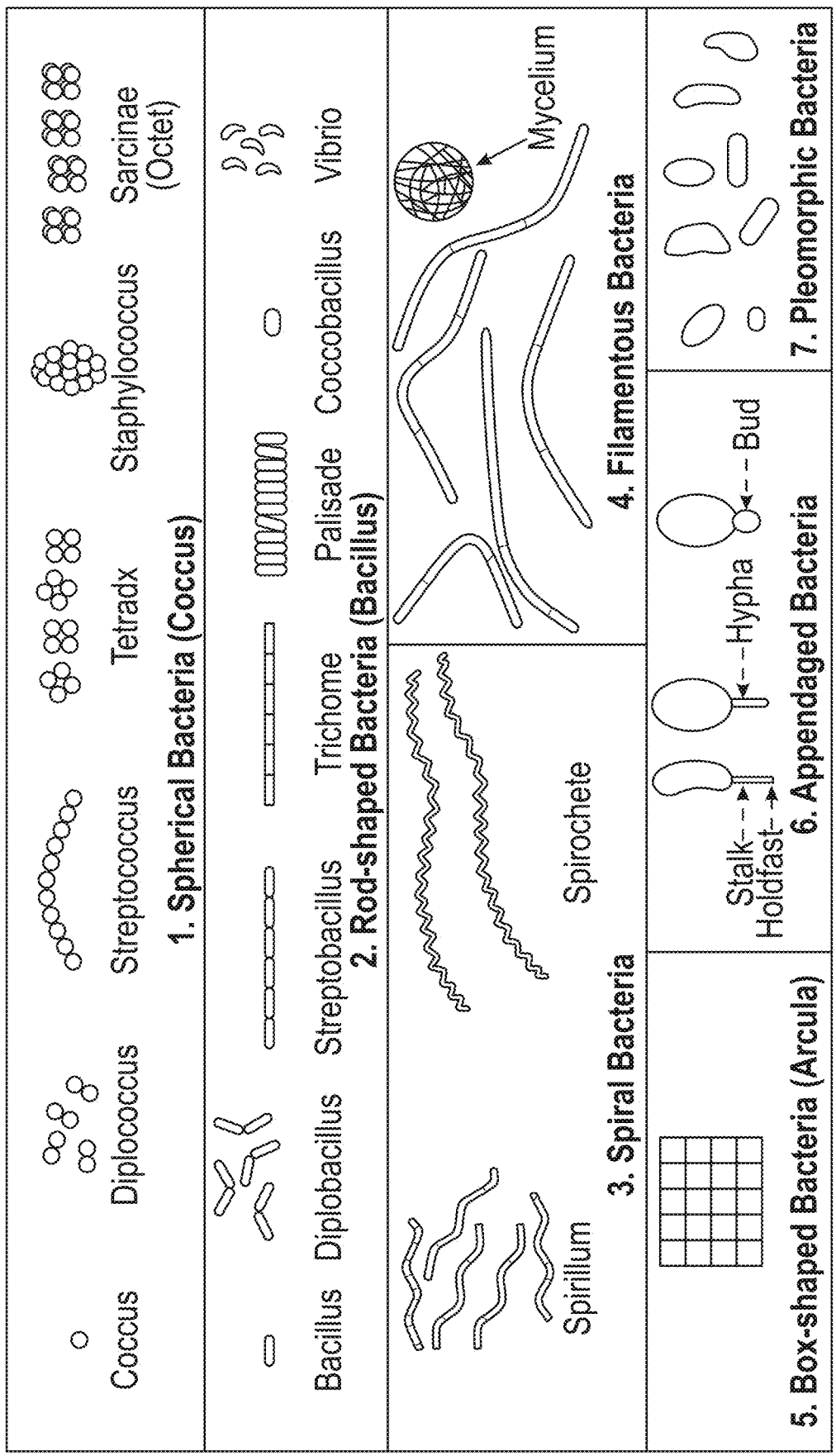
FIG. 13 is a drawing illustrating various shapes and arrangements of bacteria.

In our research we focused on these 6 types of shape of bacteria. FIG. 13 illustrates all the possible shapes and arrangement of common bacteria, including a few of the less common shapes that were not included in our research such as box shaped bacteria and appendaged bacteria. Source: https://microbiologyinfo.com/different-size-shape-and-arrangement-of-bacterial-cells.

Instead of distinguishing computers and humans apart, the bCAPTCHA will distinguish different characteristics and heuristics of bacteria. In this concept, select individuals with microbiology training are sent images of unknown or partially known species to endeavor to pin down the main characteristics of the biological samples in the digitized microscope image.

As in reCAPTCHA, the microscope images of pathogens will be subject to voting as to species type based on shape and arrangement to ensure that there is a multi-person consensus of what is contained within the image. The user could receive compensation based on the number of "correct" identifications. That is, a bCAPTCHA that agrees with the bulk of respondents would be compensated to a greater extent than those would with a lower number of "correct" identifications. This is designed to mitigate pure guessing of the results. A large-scale host site, such as Google, could be enlisted to share the queries across the globe to predetermined recipients. Special bCAPTCHA tasking could be screened to many users across the globe for specific bCAPTCHA AI use, in areas from microbiology to error analysis to mathematics, and more.

Our group has performed research into software that analyses the email and text of children and to determine if there is any explicit, suggestive, or threatening language used to detect a possible example of cyber bullying. At times, a human will be asked to "vote" as to the appropriate risk—if any—in the e-mail or text.

Figure 14:
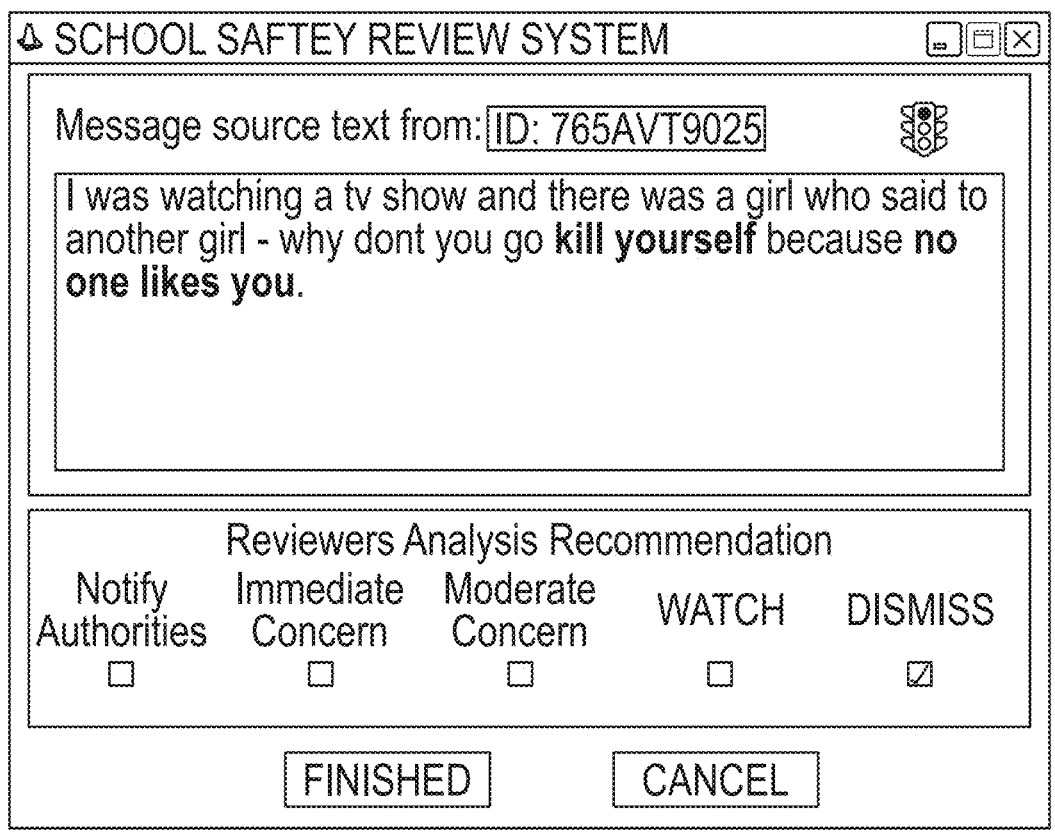
FIG. 14 is a screenshot of an anti-bullying software.

FIG. 14 is a screenshot of the Anti-Bullying software analyzing a real text. In the voting section of the child protection software, the reviewer can clearly see that the child was restating what they heard or saw in a television show and there was no threat directed at the child, so the reviewer voted to "dismiss" the alert.

Figure 15:
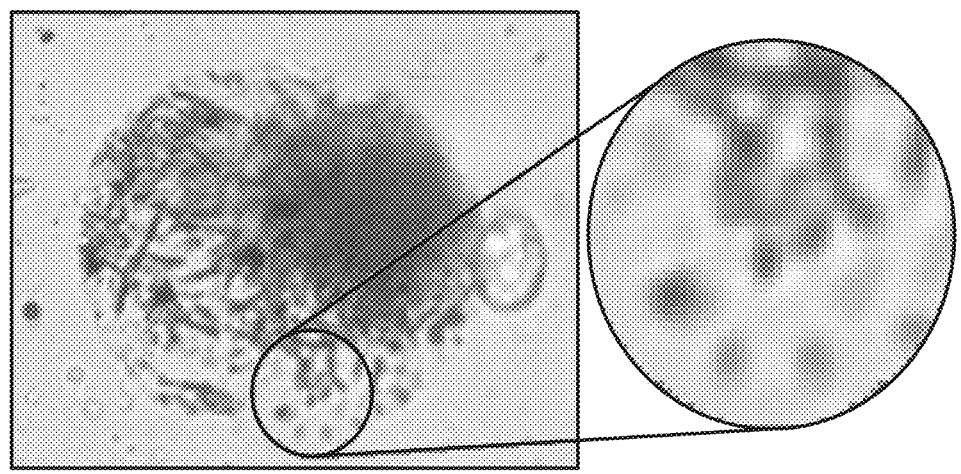

The screen for 'voting' should center on only one area of a greater field . . . users will need to see overall field to make quantitative decision as to whether the inscribed area is bacteria, pollen, dust, or a spore, etc., see FIG. 15. The field should include a reference of scale to assist. This helps the user classify based on a virus vs. larger species such as bacteria.

The average diameter of spherical bacteria is 0.5 μm–2.0 μ. For rod-shaped or filamentous bacteria, length is 1 μm–10 μm and diameter is 0.25 μm–1.0 μm.

*E. coli*, a bacillus of average size is 1.1 μm to 1.5 μm wide by 2.0 μm to 6.0 μm long *Spirochaetes* occasionally reach 500 μm in length and the cyanobacterium.

*Oscillatoria* is about 7 μm in diameter.

The bacterium, *Epulosiscium fishelsoni*, can be seen with the naked eye (600 μm long by 80 μm in diameter).

One group of bacteria, called the *Mycoplasmas*, are much smaller than these dimensions. They measure about 0.25 μm and are the smallest cells known so far. Formerly known as pleuropneumonia-like organisms (PPLO).

*Mycoplasma gallicepticum*, with a size of approximately 200 nm to 300 nm are thought to be the world smallest bacteria.

*Thiomargarita namibiensis* is world's largest bacteria, a gram-negative *Proteobacterium* found in the ocean sediments off the coast of Namibia. Usually it is 0.1 μm-0.3 mm (100 μm-300 μm) across, but bigger cells have been observed up to 0.75 mm (750 μm).

Thus a few bacteria are much larger than the average eukaryotic cell (typical plant and animal cells are around 10 μm to 50 μm in diameter). In addition to size, shape and arrangement information, additional information can be deduced to the bacteria identity by adding a gramnegative or gram-positive stain to see which bacteria are affected by the stain.

Figure 16:
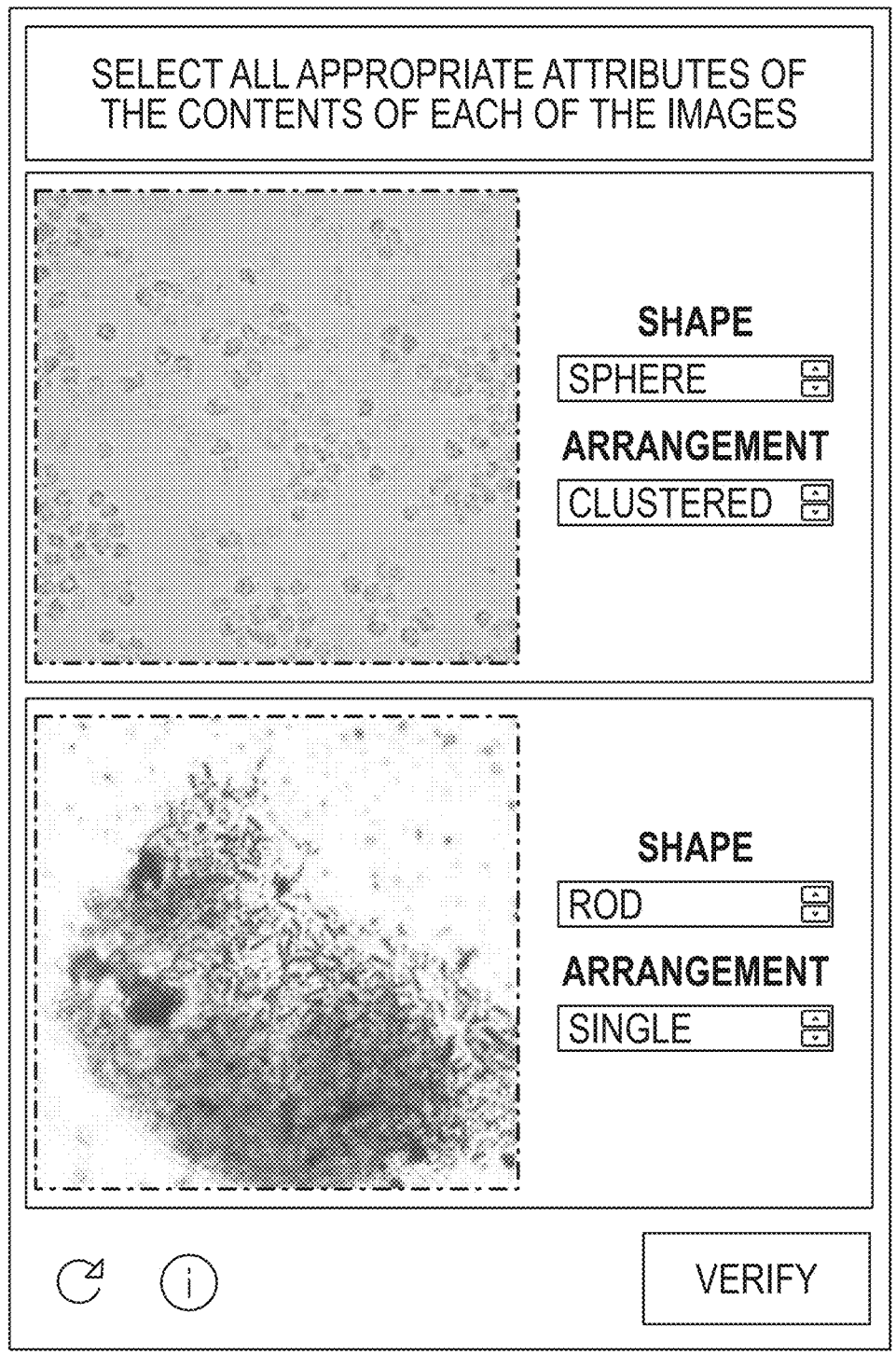
FIG. 16 is a drawing of a screenshot of a bCAPTCHA program.

FIG. 16 is a screenshot of our group's proposed bCAPTCHA program that will allow specific users who have a background in biology to examine random images for identification. As in the reCAPTCHA, one image will serve as a control image where the details as to the images shape and arrangement information has been previously established. The other image is an image that is unknown as to the shape and arrangement attributes, as well as if the image is biological in nature (bacteria, spores, pollen, etc.) or simply dust or combustion particulates. Several users will examine the same "unknown" image with a different control image, and when three users agree on the same shape and arrangement attributes, the image will be cataloged as identified.

In the preferred embodiment of the bCAPTCHA, the user will have a slider control that will allow the ability to manipulate the color, contrast, and brightness of the image to improve identification of an unknown image. The unknown and control images will then be an input function for deep machine learning.

Figure 17:
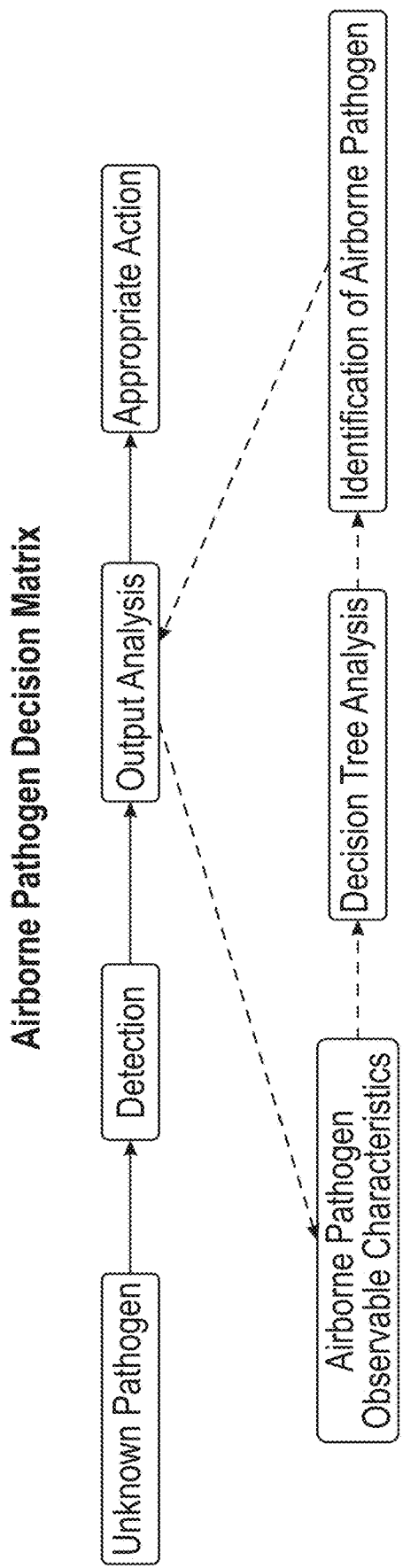
FIG. 17 is a flowchart illustrating a decision tree for a bCAPTCHA process.

FIG. 17 is a flowchart illustrating a Decision Tree Method. The CAPTCHA process is designed to complement the decision matrix, and improve machine learning to yield increasing microorganism identification accuracy. In the process we have developed, the decision matrix begins broad and truncates using a lookup table consisting of key elements of known bacterial morphological characteristics.

FIG. 18 is drawing of a screenshot showing a match for a gram stain;

FIG. 19 is a drawing of a screenshot showing a match for an arrangement;

FIG. 20 is a drawing of a screenshot showing a match for an flagella or cilia;

FIG. 21 is a drawing of a screenshot showing a match for a type of cilia;

FIG. 22 is a drawing of a screenshot showing a not applicable for a type of flagella;

FIG. 23 is a drawing of a screenshot showing a match for an *Acinetobacter baumannii*;

The decision matrix, may be programmed as an Excel lookup table.

One embodiment of the programming specific to bacteria, may be as follows:

Begin a broad morphological search, and become progressively more specific

Figure 24:
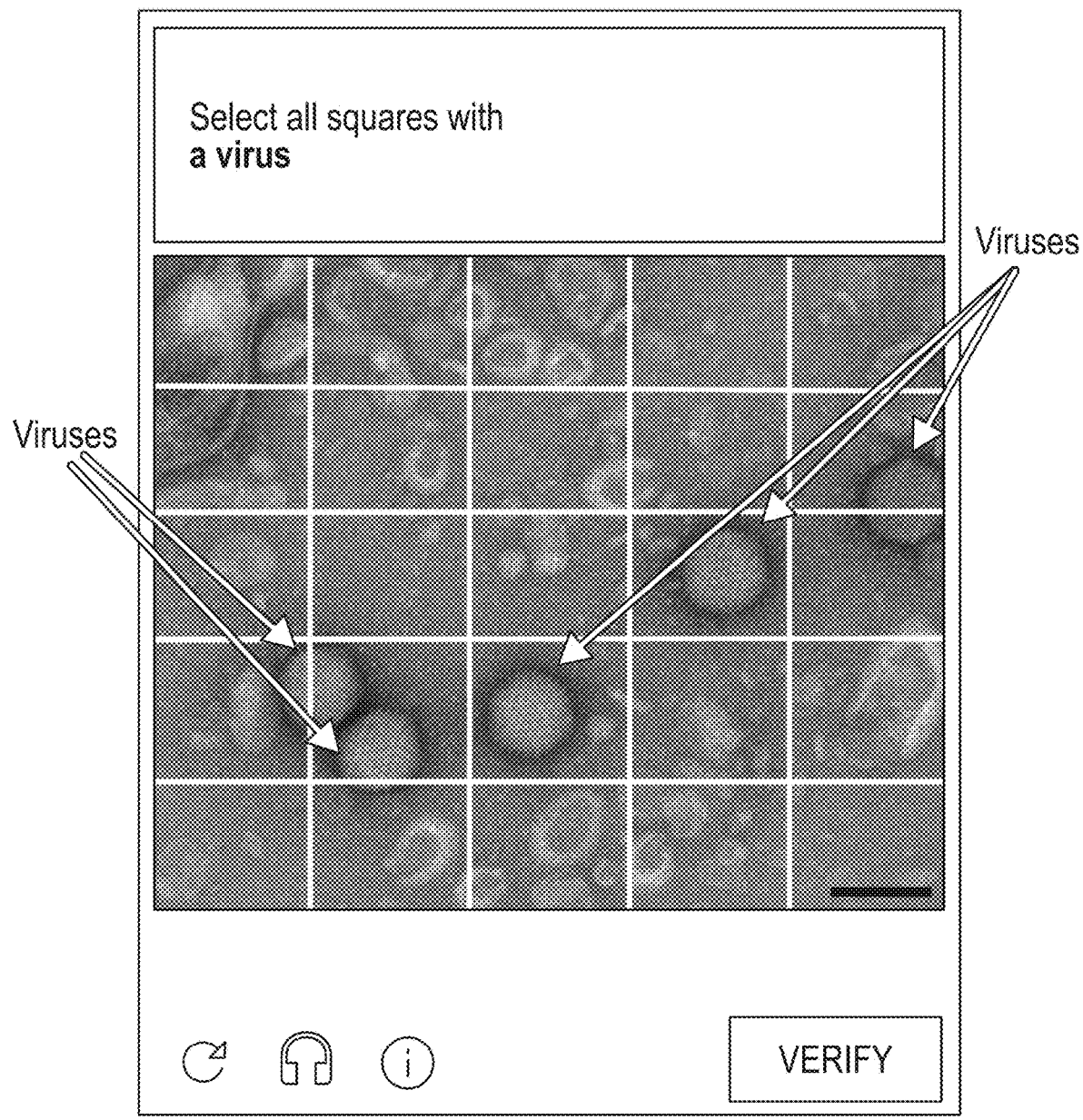
FIG. 24 is a drawing of a bCAPTCHA screen for selecting a virus.

Identify categories are placed order
1. Gram Stain—a very broad category with only 2 options, Negative and Positive
2. Presence or Absence of Capsule—very broad with only 2 options, Present or Absent
3. Shape—becomes less broad with 5 options—Coccus, Bacillus, Coccobacillus, Spiral, and Filamentous
4. Arrangement—becomes more specific with 6 options— Mono, Staph, Pleo, Strep, Tetrad, and Diplo
5. Flagella or Cilia—also a broad category that has only 4 options—Flagella, Cilia, Both, and None Another set of preferred embodiments of the disclosed invention is shown in the following three bCAPTCHA screens, see FIGS. 24, 25, and 26. The user is prompted to select squares in the photograph the display parts of a bacteria or virus. In other versions, the user might be asked to select what classification of bacteria or virus is displayed, or even the users best guess from a select list what the microorganism is by name.

Figure 25:
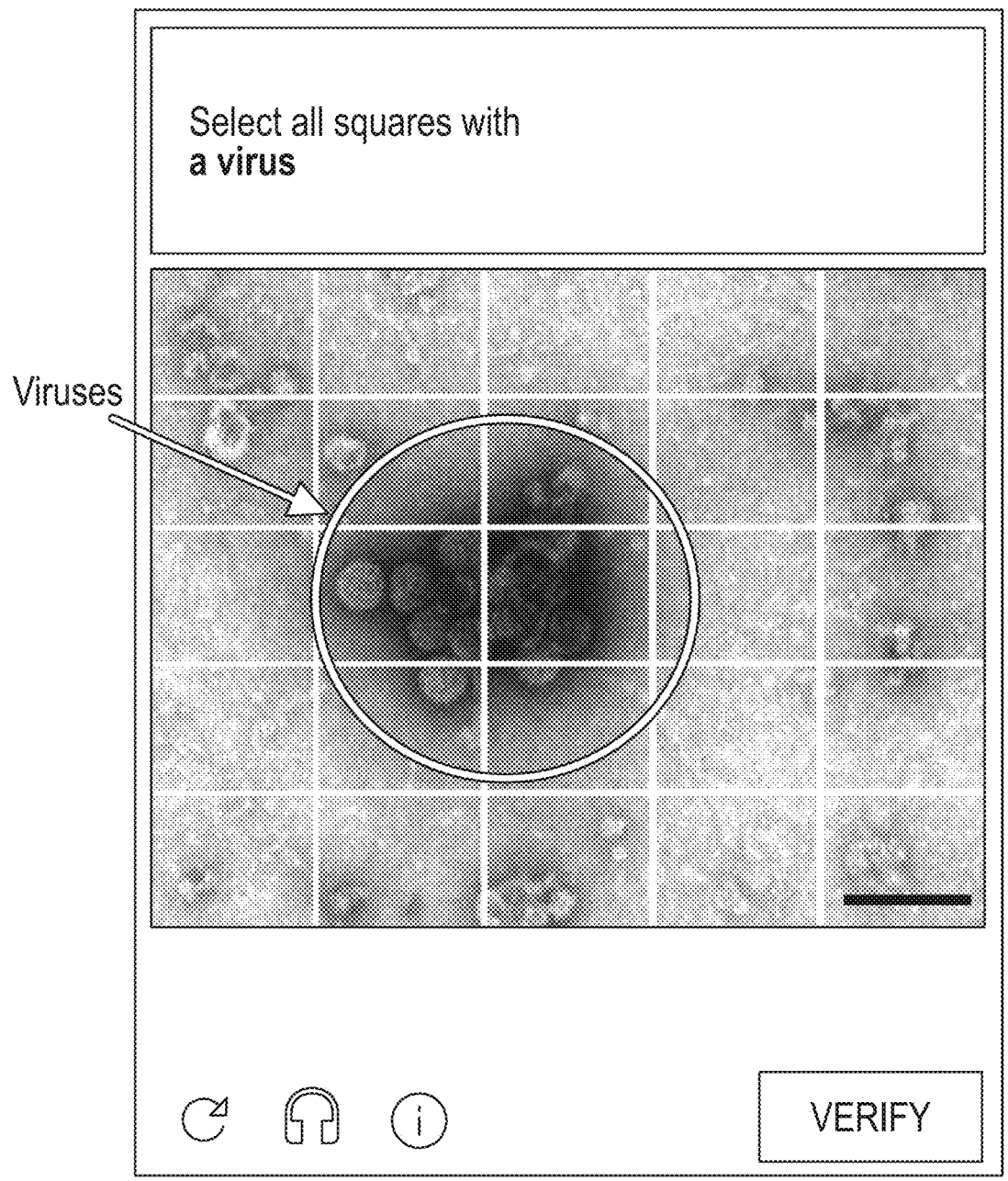
FIG. 25 is a drawing of a bCAPTCHA screen for selecting a virus in noise.

FIG. 25 shows an example of a bCAPTCHA viral identification in a noise filled field.

Figure 26:
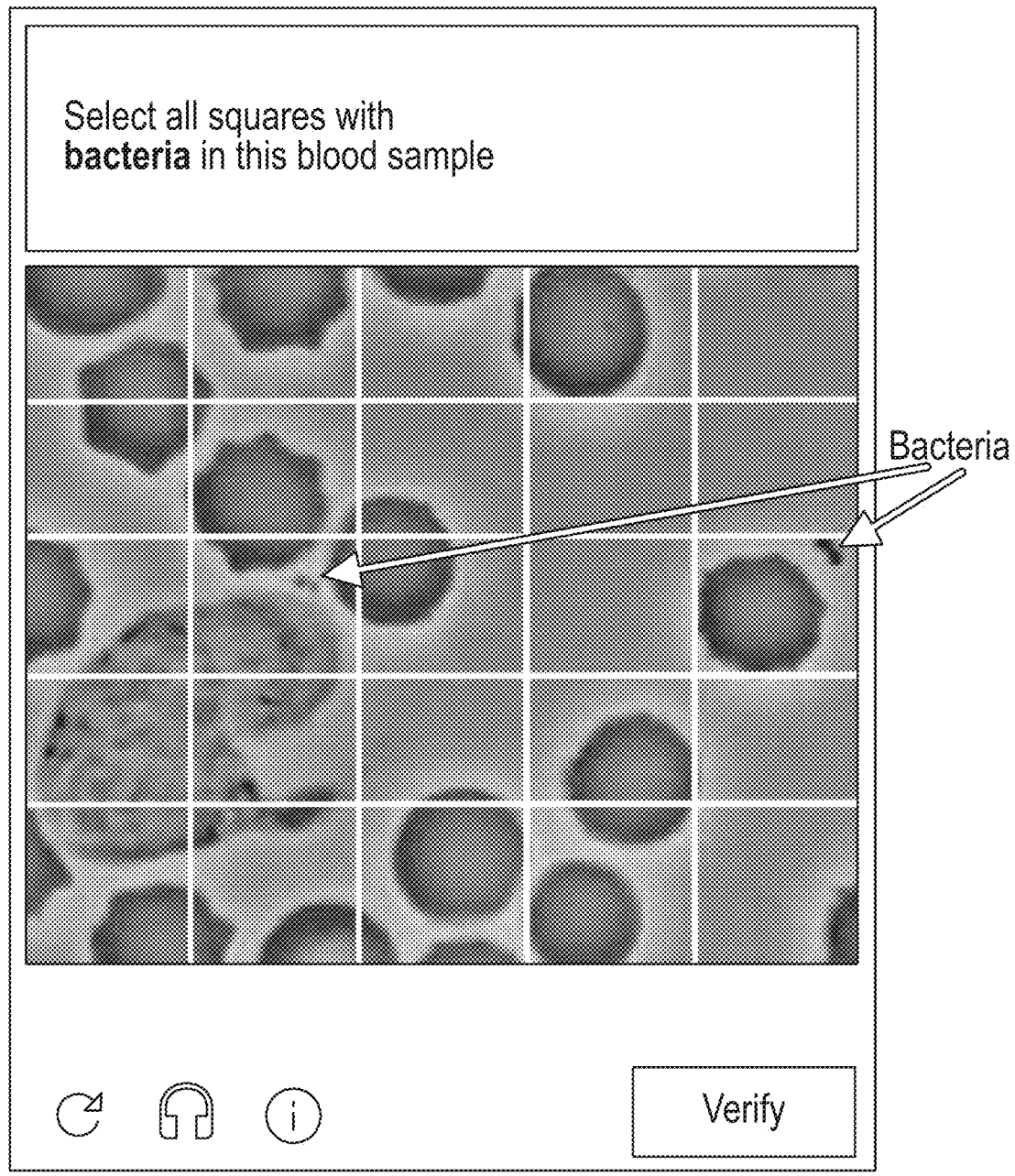
FIG. 26 is a drawing of a bCAPTCHA screen for selecting a bacteria in a blood sample.

FIG. 26 shows an example of a bCAPTCHA identifying bacteria in a field of normal blood cells.

The research conducted demonstrates that a simple decision tree matrix can be employed to achieve a high probability of correct pathogen identification, as long as the system incorporates machine learning to improve the discrimination of select morphological characteristics required for pathogen classification. The bCAPTCHA method addresses the role of AI input to facilitate such machine learning requirements.

The disclosed a microbiological captcha to improve artificial intelligence pathogen identification has many advantages. It can assist in training AI to identify many different pathogens, including bacterial and viral pathogens. The disclosed invention can use the power of many people to assist in AI learning.

It should be noted that the terms "first", "second", and "third", and the like may be used herein to modify elements performing similar and/or analogous functions. These modifiers do not imply a spatial, sequential, or hierarchical order to the modified elements unless specifically stated.

The essential feature of the disclosed invention is the use of the CAPTCHA process previously employed by those skilled in the art to identify a human verses machines operator, in a new application to utilize the ability of a human operator to classify pathogen images in a complex image background, so as to yield data sets for neural network learning. In order to improve the accuracy of image identification, especially with convolutional neural networks, the neural network program much be provided with examples of desired image features to be parsed from the images and identified or classified. As such, image fields should contain both image objects the user desires to be identified, as well as background artifacts or other objects that are not of interest to the end user. For the purposes of the disclosed invention, images of pathogens, which include preferably viruses, bacteria, fungi, or spores, are presented to a human user preferably from actual microscopic photos or video databases, or which may be parsed from any number of research papers obtained from the internet. The images may derived from electron microscopy or optical microscopy or other forms of microscopy. The preferred objective is to present an image to a human operator where the desired feature or pathogen is known, as to type, classification, and geographic position in the image, and then to interrogate the human operator to provide their own identification of the pathogen or other target biological feature for type, classification, and position. The combination of previously known and human operator data may now be introduced to a neural network for image processing and subsequent leaning.

While the disclosure has been described with reference to several embodiments, it will be understood by those skilled in the art that various changes may be made, and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiments disclosed as the best mode contemplated for carrying out this disclosure, but that the disclosure will include all embodiments falling within the scope of the appended claims.

What is claimed is:

1. A method of testing identification of pathogens using a biological Completely Automatic Public Turing Test To Tell Humans And Computers Apart (bCAPTCHA) system, the method comprising:
   automatically presenting a first electronic image for a participant with a computing system, wherein said electronic image comprises an image of a biological pathogen;
   presenting options for the participant to select from, and to identify characteristics of the pathogen;
   processing selected options from the participant; and
   providing a slide control to the participant to allow the participant to manipulate the color, contrast, and/or brightness of the image.

2. The method of claim 1, wherein the presenting options act comprises:
   presenting several pathogen shapes for the participant to select one of.

3. The method of claim 2, where the several pathogen shapes are selected from the group consisting of rod type, spherical type, spiral type, filament type, intermediate spherical and rod type, and pleomorphic type.

4. The method of claim 1, wherein the presenting options act comprises:
   presenting several bacteria shapes for the participant to select one of.

5. The method of claim 1, wherein the presenting options act comprises:
   presenting several virus shapes for the participant to select one of.

6. The method of claim 1, wherein the presenting options act comprises:
   presenting several pathogen arrangement types for the participant to select one of.

7. The method of claim 6, where the several pathogen arrangement types are selected from the group of single, paired, chains, group of four, and grape like cluster.

8. The method of claim 1, further comprising:
   automatically presenting a second electronic image for the participant with a computing system, wherein said electronic image comprises a detail of the first image and indication of the scale of the second and first images.

9. The method of claim 1 further comprising:
   providing the processed responses to an AI system to facilitate the AI's learning of identifying biological pathogens.

10. A method of testing identification of pathogens using a biological Completely Automatic Public Turing Test To Tell Humans And Computers Apart (bCAPTCHA) system, the method comprising:
    automatically presenting a first electronic image for a participant with a computing system, wherein said electronic image comprises an image of a biological pathogen;
    presenting options for the participant to identify the pathogen;
    processing selected options from the participant; and
    providing a slide control to the participant to allow the participant to manipulate the color, contrast, and/or brightness of the image.

11. The method of claim 10, wherein the image is divided into a plurality of a squares; and the presenting options act comprises:
    presenting an option to select which squares of the image contain at least one biological pathogen.

12. The method of claim 10, wherein the image comprises image noise and the image is divided into a plurality of a squares; and the presenting options act comprises:
 presenting an option to select which squares of the image contain at least one biological pathogen.

13. The method of claim 10, wherein the image shows a plurality of non-pathogen cells and at least one biological pathogen, and the image is divided into a plurality of a squares; and the presenting options act comprises:
 presenting an option to select which squares of the image contain at least one biological pathogen.

14. The method of claim 10, wherein the biological pathogen is a bacteria.

15. The method of claim 10, wherein the biological pathogen is a virus.

* * * * *